United States Patent
Miller et al.

[11] Patent Number: 5,784,151
[45] Date of Patent: Jul. 21, 1998

[54] APPARATUS FOR TESTING A PULSED LIGHT OXIMETER

[75] Inventors: Mark Edward Miller, Vancouver; Ronald William Evans, Delta, both of Canada

[73] Assignee: Datrend Systems Inc., British Columbia, Canada

[21] Appl. No.: 754,042

[22] Filed: Dec. 3, 1996

[51] Int. Cl.[6] .................................................. A61B 5/00
[52] U.S. Cl. .................................................. 356/41; 600/330
[58] Field of Search .................................. 356/41; 128/633; 250/252.1; 600/330

[56] References Cited

U.S. PATENT DOCUMENTS

| | | | |
|---|---|---|---|
| 4,796,633 | 1/1989 | Zwirkoski | 128/634 |
| 4,968,137 | 11/1990 | Yount | 356/41 |
| 5,166,517 | 11/1992 | Volgyesi | 250/252.1 |
| 5,348,005 | 9/1994 | Merrick et al. | 128/633 |

FOREIGN PATENT DOCUMENTS 2280024  1/1995  United Kingdom ............ 128/633

OTHER PUBLICATIONS

K. Tremper & S. Barker, "Pulse Oximetry", Anesthesiology, vol. 70; pp. 98-108, 1989.

*Primary Examiner*—Richard A. Rosenberger

[57] ABSTRACT

The invention relates to apparatus for testing a pulsed light oximeter, such as a non-invasive oximeter which emits pulses of red and infrared light. A light sensor produces an electrical pulse signal representative of light flashes emitted by the oximeter, and a signal generator produces a plurality of absorbance signals representative of the optical absorbance of an anatomical part at the wavelength of each light flash. A signal selector responds to time interval, duration and amplitude features of the electrical pulse signal, or to electrical signals produced by the oximeter itself, and thereby selects one of the plurality of absorbance signals to produce a selected absorbance signal. The selected absorbance signal is converted to light and conveyed to the oximeter to simulate the effect of the anatomical part on the light flashes emitted by the oximeter. The selector additionally produces an alarm signal if features of the electrical pulse signal do not match predefined reference features derived from a priori knowledge of the oximeter. The invention also includes a novel probe for use in testing an oximeter with a transilluminating sensor, the probe incorporating two prisms with each prism having one end in the shape of an acute wedge to achieve a low profile. The wedges of both prisms have roughened surfaces to scatter light so that the probe advantageously obtains a low position sensitivity. The invention may also be incorporated into the oximeter itself, advantageously providing the oximeter with self-diagnostic capability.

33 Claims, 17 Drawing Sheets

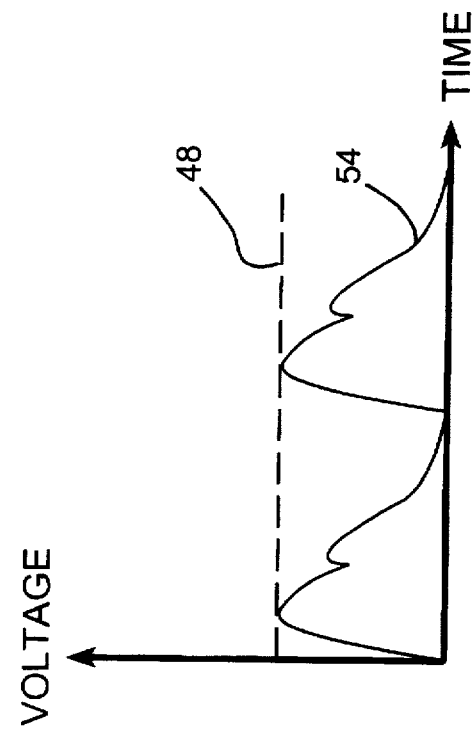
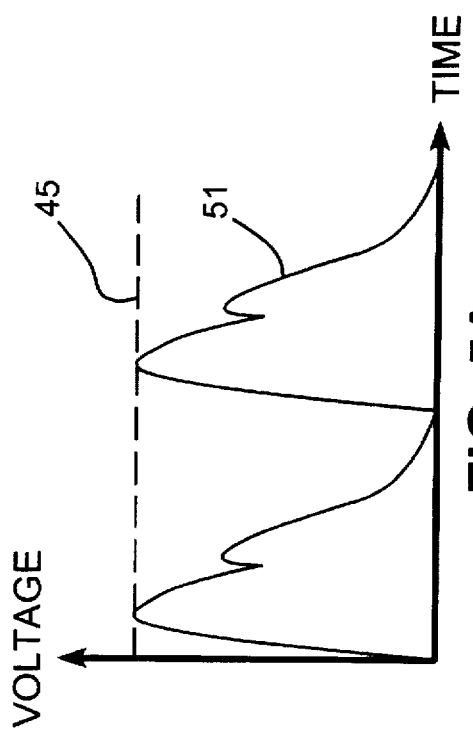
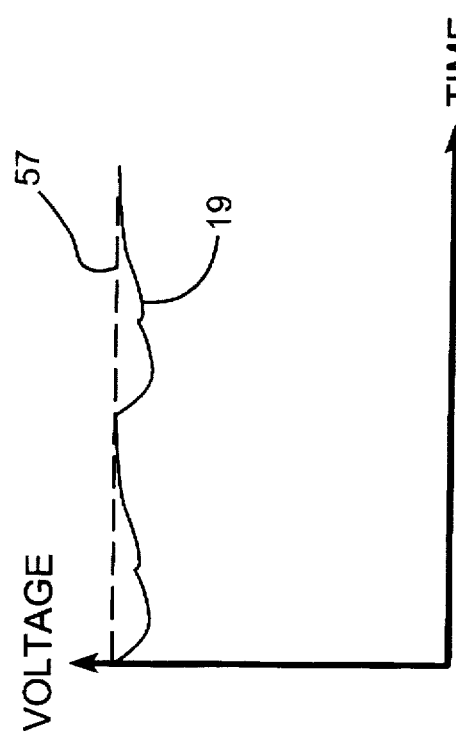

APPARATUS FOR TESTING A PULSED LIGHT OXIMETER

FIELD OF THE INVENTION

The present invention generally relates to the field of pulsed light spectrophotometers, and more particularly, relates to apparatus for the testing or calibration of pulse oximeters, a particular implementation of the pulsed light spectrophotometric principle.

BACKGROUND OF THE INVENTION

A measure of the total net effect of respiration can be obtained by determining the concentration of oxygen and carbon dioxide in the blood. Oxygen content is normally measured in millimeters of mercury and is referred to as the partial pressure or tension of oxygen. At a given level of oxygen tension, a specific amount of oxygen is bound to hemoglobin in the blood to form oxyhemoglobin. The percentage of oxyhemoglobin in the blood is referred to as the oxygen saturation level.

Blood oxygen levels were first measured using a Clark electrode on a sample of blood removed from a patient. An improvement to the Clark electrode was the use of spectrophotometric techniques on a much smaller blood sample. This method measured the oxygen saturation level in the blood by correlating the optical absorbance of various components of blood at several wavelengths of light. Continuous invivo measurements of blood oxygen saturation were obtained using the spectrophotometric principle by placement of an optical fibre catheter in the arterial vessels of the body.

In 1976, the spectrophotometric technique was extended to a non-invasive procedure by Merrick and Hayes who described a device which used eight wavelengths to correlate optical absorbance of the ear lobe to oxygen saturation level, taking into account tissue, cartilage and other non-blood products encountered between the light transmitter and detector. This approach was commercialized by Hewlett-Packard of Waltham MASS as the Hewlett-Packard Ear Oximeter. Improvements to this technique resulted in the development of the two-wavelength "pulse oximeter" which is in common use today. The use of only two wavelengths simplifies the construction of the pulse oximeter, making it an affordable and effective device for monitoring oxygen saturation levels in all areas of patient care.

The pulse oximeter relies on measurement of the absorption of light transmitted through or reflected from a part of the body, this absorption having a varying component created by the presence of pulsing blood and a nonvariable component resulting from the presence of skin, tissue and other non-blood body components. The varying (AC) and nonvarying (DC) components of the absorbance at each wavelength can be separated and measured, and the ratio of the AC to the DC component derived to obtain a normalized absorbance, thereby compensating for variations in the incident light intensity. In a two-wavelength pulse oximeter, the ratio of normalized absorbances A at wavelengths L1 and L2 is then obtained as:

$$A_{L1}/A_{L2} = [AC_{L1}/DC_{L1}]/[AC_{L2}/DC_{L2}]$$

This ratio, depending on the wavelengths chosen, allows the determination of several parameters of interest in the blood. The particular parameter of interest for the case of the pulse oximeter is the blood oxygen saturation.

Deriving the above ratio requires a method of discriminating wavelengths of light received from the illuminated subject. In the pulsed light spectrophotometric method, the wavelengths of interest are generated one at a time in a predefined sequence by the light source of the oximeter. The subject is therefore exposed to only one wavelength of light at any given instant. Light received from the subject is then demultiplexed to reconstruct the absorbances at each wavelength, using timing information derived from the sequencing of the wavelengths at the source. The eight-wavelength oximeter of Merrick and Hayes implemented the pulsed light method by passing white light through eight optical filters which were equally spaced around the circumference of a motor-driven wheel. The pulse oximeter achieves a similar result at two wavelengths typically by using red and infrared light emitting diodes which are alternately switched on and off in a predetermined activation sequence.

The Hewlett-Packard Ear Oximeter and the pulse oximeter are only two of many possible implementations of the pulsed light spectrophotometric technique. By correct selection of the various wavelengths of light, blood components in addition to oxyhemoglobin can also be detected. For example, Hamamatsu Corporation of Bridgewater N.J. utilizes four wavelengths of pulsed light to detect deoxygenated hemoglobin, oxygenated hemoglobin and cytochrome aa3 in its NIRO-500 Cerebral Oxygenation Measuring System. Abbott Laboratories Inc. of Mountain View Calif. uses three wavelengths of pulsed light in their invivo, catheter-based Oximetrix 3 oximeter in order to improve the accuracy of oxygen saturation measurement.

A well-documented failure mode for spectrophotometric oximeters in the clinical environment concerns the sensor or fibre optic cable by which light pulses are conveyed to and received from the patient. Such failures are often not obvious to clinical staff and may lead to inaccurate saturation measurements, and as a result, inappropriate choices of patient treatment. Without a standardized test instrument these and other failures are difficult to identify, emphasizing the need for adequate test methods.

The inventions disclosed by Yount in U.S. Pat. No. 4,968,137 and Volgyesi in U.S. Pat. No. 5,166,517 are examples of prior art devices which address the need for testing or calibrating two-wavelength pulse oximeters. Such prior art testers employ an oxygenated blood sample or a liquid material of comparable optical properties which is inserted in the light path of the oximeter to simulate the absorbance of the part of the body which would normally be transilluminated. Various means are utilized to produce the time-varying (AC) component of the absorbance which is necessary to obtain an oxygen saturation indication on the pulse oximeter. Yount discloses rotating polarizing filters or a reciprocating wedge of absorbing material to achieve an absorbance having static and time-varying components. A similar result is achieved by the device disclosed by Volgyesi wherein manual compression of a member adjacent to an absorbing liquid within the device produces the required time-varying component of the absorbance.

A disadvantage of the prior art device described by Yount is that the optically absorbant substance placed in the light path of the pulse oximeter is sheep's or human blood of a predefined oxygen saturation. Blood having a predefined saturation may be difficult to stabilize for extended periods of time, and furthermore may be potentially dangerous to handle. A limitation of the prior art device described by Volgysei is that the saturation indicated by the oximeter in response to use of the device cannot be easily varied without changing the composition of the liquid sample within the device. Furthermore, inventions as disclosed by Yount and Volgyesi respectively do not provide means responsive to the sequence of light flashes produced by the oximeter being tested or calibrated. Therefore, despite what may appear to be an acceptable saturation indication on the oximeter in response to the use of such prior art test devices, the devices cannot determine if the oximeter is functioning normally according to its design.

An alternate class of test devices which simulate the optical absorbance of a part of the body by wholly electronic means provide some advantages over the devices described above. The advantage of electronic simulators over prior art relying on absorbant material inserted in the light path of the oximeter is that parameters such as the magnitude of the absorbance or the frequency of the time-varying component may be easily varied through the use of readily-controlled electrical signals.

Examples of such electronic simulators include simple signal generators often supplied by the manufacturers of pulse oximeters to test the function of the electronic portion of their respective products. Such generators, however, are of limited usefulness in that function and calibration of the sensor component of the oximeter is not verified. This is a significant limitation since in practise it is the oximeter sensor which is most likely to fail due to extended use in the clinical environment.

An example of a prior art device using electronic means to simulate living tissue is described by Merrick et al in U.S. Pat. No. 5,348,005. Merrick et al disclose apparatus intended for testing two-wavelength pulse oximeters using two photodiodes to detect the light flashes emitted by the pulse oximeter sensor. The photodiodes are mounted in a probe of shape similar to a human digit over which the sensor of the pulse oximeter is applied. Electrical signals produced by the two photodiodes are electronically modulated and used to drive a bar of light emitting diodes (LEDs) which illuminate the detector of the oximeter. The apparatus is configured so that the oximeter responds to the modulated light from the LEDs as it would to light modulated by the time-varying absorbance of living tissue.

A significant practical limitation of the invention disclosed by Merrick et al is that the device is strictly limited to the case of the two-wavelength pulse oximeter in which one of the wavelengths is that of red light, and the other wavelength is that of infrared light. Such a device cannot be easily modified to test oximeters which use more than two wavelengths of light, nor can the device test oximeters which use two visible wavelengths of light. Furthermore, due to the limitations of optical discrimination employed, it would be impractical to implement the invention of Merrick et al for the case of existing multi-wavelength pulsed light oximeters, such as the Hewlett-Packard Ear Oximeter, the Hamamatsu NIRO-500, and Abbott Laboratories Oximetrix 3 mentioned above, where the wavelength separation may be as little as 25 nanometers. Although pulse oximeters currently employ only two wavelengths, Tremper and Barker in "Pulse Oximetry" (Anesthesiology V. 70 pp. 98–108, 1989) show that a minimum of four wavelengths are in fact required to distinguish other species of hemoglobin, such as carboxyhemoglobin and methemoglobin, which are present under certain pathological conditions. Therefore, it is foreseeable that future pulse oximeters may employ more than two wavelengths to distinguish these pathologic hemoglobins from oxyhemoglobin, and thereby eliminate a source of error which plagues present day pulse oximeters. The apparatus of Merrick et al will not be useable with such future pulse oximeters.

A further limitation of the invention disclosed by Merrick et al concerns the probe to which the pulse oximeter sensor is applied. Merrick et al describe a probe comprising a shell in the shape of a digit containing the optical sensing and emitting elements which respectively are used to detect light from and transmit light to the oximeter sensor. The probe operates efficiently only if the oximeter sensor is positioned in the correct orientation and precisely over the appropriate optical elements within the probe. A further limitation of the probe is that no means are provided to assist the operator in positioning the oximeter sensor in the correct orientation.

A limitation of all prior art described above is that no means have been suggested which respond to the features of the light flashes produced by the oximeter, such as the time interval between, the duration of, or the amplitude of the individual flashes of light. Therefore, prior art devices provide only the most indirect indication, namely the oxygen saturation displayed by the oximeter, for determining whether or not the oximeter is functioning normally according to its design.

To overcome some of the limitations of the prior art, an object of the present invention is to provide apparatus for testing a pulsed light oximeter, the apparatus having one broadband detector which produces electrical pulses in response to light flashes emitted by the oximeter. A signal selector responds to the time interval between, the duration of, or the amplitude of the electrical pulses, and discriminates the various wavelengths of light emitted by the oximeter, based on a priori knowledge of the oximeter under test. As the oximeter produces a light flash at a particular wavelength, the selector selects one of several absorbance signals representative of the absorbance of an anatomical part at that wavelength, each absorbance signal being preselected to produce a predefined oxygen saturation indication on the oximeter. The selected absorbance signal is converted to light and radiated to the oximeter to simulate the effect of the anatomical part on the light flash. Unlike approaches which rely on optical discrimination of wavelengths, this approach may be advantageously embodied to suit oximeters which emit a multiplicity of arbitrary wavelengths.

A further object of the present invention is to provide apparatus for testing a pulsed light oximeter, the apparatus having one optical detector and means responsive to the features of electrical pulses produced by the detector to produce an alarm signal if the features do not match predefined reference features derived from a priori knowledge of the oximeter. This, in combination with the oxygen saturation displayed by the oximeter in response to the apparatus, advantageously provides a definitive indication that the oximeter is functioning normally according to its design.

A further object of the present invention is to provide a probe having the advantage of low position sensitivity for use in testing an oximeter with a transilluminating sensor. The probe includes an optical detector, an optical emitter and two prisms, one prism conducting light from the sensor to the detector, and the other conducting light from the emitter to the sensor. One end of each prism is in the shape of a highly acute wedge with a roughened exterior which scatters light throughout the wedge. The prisms thereby advantageously achieve a large and diffusive optical surface for the detection or emission of light. The shell of the probe contains the prisms and provides a barrier to prevent light transmission between them, and between the light emitting and light detecting elements of the sensor itself. The signal produced by the optical detector is displayed to the operator, and a second light detector located near the optical emitter of the probe produces an alarm signal should the oximeter sensor be inadvertently applied to the probe in an inverted position. These features advantageously provide the operator with a means for correctly orienting the sensor on the probe.

An additional object of the present invention is to provide apparatus for testing a pulsed light oximeter, the oximeter having light emitting diodes, or LEDs, activated by corresponding electrical drive signals. The test apparatus in this case includes a signal generator which produces several absorbance signals representative of the absorbance of an anatomical part at the wavelength of light emitted by each LED. Selecting means responds to the electrical drive signals and selects the appropriate absorbance signal for each LED when the LED is activated. The selected absorbance signal is converted to light and radiated to the oximeter to simulate the effect of the anatomical part on the light emitted by the LED. The test apparatus also includes an optical detector which produces electrical pulses in response to light flashes produced by the LEDs, and comparison means is included to produce an alarm signal if electrical pulses from the detector do not correspond to the drive signals which activate the LEDs. Advantageously, this test apparatus may be incorporated into the oximeter itself to achieve an improved oximeter with enhanced self-diagnostic capabilities.

The applicants are aware of the following United States Patents which are more or less relevant to the subject matter of the applicants' invention.

| 5,348,005 | 07/1994 | Merrick et al | 128/633 |
| 4,968,137 | 11/1990 | Yount | 128/634 X |
| 5,166,517 | 11/1992 | Volgysei | 250/252.1 |
| 4,796,633 | 01/1989 | Zwirkoski | 128/634 |

SUMMARY OF THE INVENTION

The invention is directed toward apparatus for testing a pulsed light oximeter, comprising: light sensing means for producing an electrical pulse signal representative of light flashes emitted by the oximeter, each light flash emitted having one of a plurality of predefined wavelengths; signal generating means for producing a plurality of absorbance signals representative of the optical absorbance of an anatomical part at the wavelength of each light flash; selecting means responsive to one or more features of the electrical pulse signal for selecting one of the plurality of absorbance signals to produce a selected absorbance signal; and light radiating means responsive to the selected absorbance signal for radiating light to the oximeter to simulate the effect of the anatomical part on the light flashes emitted by the oximeter. The features responded to singly or in combination include the time interval between, the duration of, or the amplitude of individual pulses which comprise the electrical pulse signal. The selecting means of the apparatus further includes means for producing an alarm signal if features of the electrical pulse signal do not match predefined reference features derived from a priori knowledge of the oximeter.

The amplitude of each absorbance signal is preselected to produce a predefined oxygen saturation indication on the oximeter, each absorbance signal consisting of a static component representative of tissue and venous blood in the anatomical part, and a time-varying component representative of arterial blood flow through the anatomical part. If the oximeter is a two-wavelength pulse oximeter, the absorbance signals generated would consist of the absorbance of the anatomical part near the wavelength of red light, and the absorbance of the anatomical part near the wavelength of infrared light.

The invention is further directed toward a probe for use in testing an oximeter having a transilluminating sensor with light emitting and light detecting elements, comprising: a light sensing means for producing a detected light signal representative of light emitted by the sensor; a prism for conducting light from the emitting element to the light sensing means, the prism having refractive index greater than air and having one end in the shape of an acute wedge, the wedge having a roughened surface to scatter throughout the wedge the light impingent upon it from the emitting element; a light radiating means for producing light in response to a signal representative of light to be received by the sensor; a prism for conducting light produced by the radiating means to the detecting element, the prism having refractive index greater than air and having one end in the shape of an acute wedge, the wedge having a roughened surface to disperse over the detecting element the light conducted from the radiating means; and a shell for containing the prisms, substantially in the shape of an anatomical part, and including two internal cavities open at the distal end to receive the wedges of the prisms, the cavities separated by a barrier to prevent light transmittance between the radiating and sensing means, and between the prisms. Additionally, the barrier prevents light transmittance between the light emitting and light detecting elements of the sensor. A light sensitive element located proximal to the radiating means produces an alarm signal should the sensor be applied to the probe with incorrect orientation. Display means are included for displaying the detected light signal to an operator.

The invention is additionally directed toward apparatus for testing a pulsed light oximeter which emits light flashes, each light flash having one of a plurality of predefined wavelengths, comprising: light sensing means for producing a synchronization signal representative of light flashes emitted at one of the predefined wavelengths; signal generating means for producing a plurality of absorbance signals representative of the optical absorbance of an anatomical part at the wavelength of each light flash; selecting means responsive to the synchronization signal for selecting one of the absorbance signals to produce a selected absorbance signal; and light radiating means responsive to the selected absorbance signal for radiating light to the oximeter to simulate the effect of the anatomical part on the light flashes emitted by the oximeter.

The invention is also directed toward apparatus for testing a pulsed light oximeter incorporating light emitting devices activated by electrical drive signals, each device emitting a light flash of predefined wavelength in response to a corresponding drive signal, comprising: signal generating means for producing a plurality of absorbance signals representative of the optical absorbance of an anatomical part at the wavelength of each light flash; selecting means responsive to the electrical drive signals for selecting one of the absorbance signals to produce a selected absorbance signal; light radiating means responsive to the selected absorbance signal for radiating light to the oximeter to simulate the effect of the anatomical part on the light flashes emitted by the oximeter; light sensing means for producing a detected light signal representative of light flashes emitted by the oximeter; and comparison means for comparing the detected light signal with the electrical drive signals. If the oximeter is a pulse oximeter, the invention may advantageously comprise a part of the pulse oximeter.

BRIEF DESCRIPTION OF THE DRAWINGS

FIGS. 5A, 5B, 5C and 5D are waveform diagrams illustrating the signals produced by the absorbance signal generator of the invention.

DESCRIPTION OF THE PREFERRED EMBODIMENT

The embodiment illustrated herein is not intended to be exhaustive or to limit the invention to the precise form disclosed. It is chosen and described in order to explain the principles of the invention, and its application and practical use for the case of the two-wavelength pulse oximeter so that others skilled in the art may utilize the invention. The application and extension to pulsed light spectrophotometers utilizing more than two wavelengths of light should be obvious to those skilled in the art.

Figure 1:
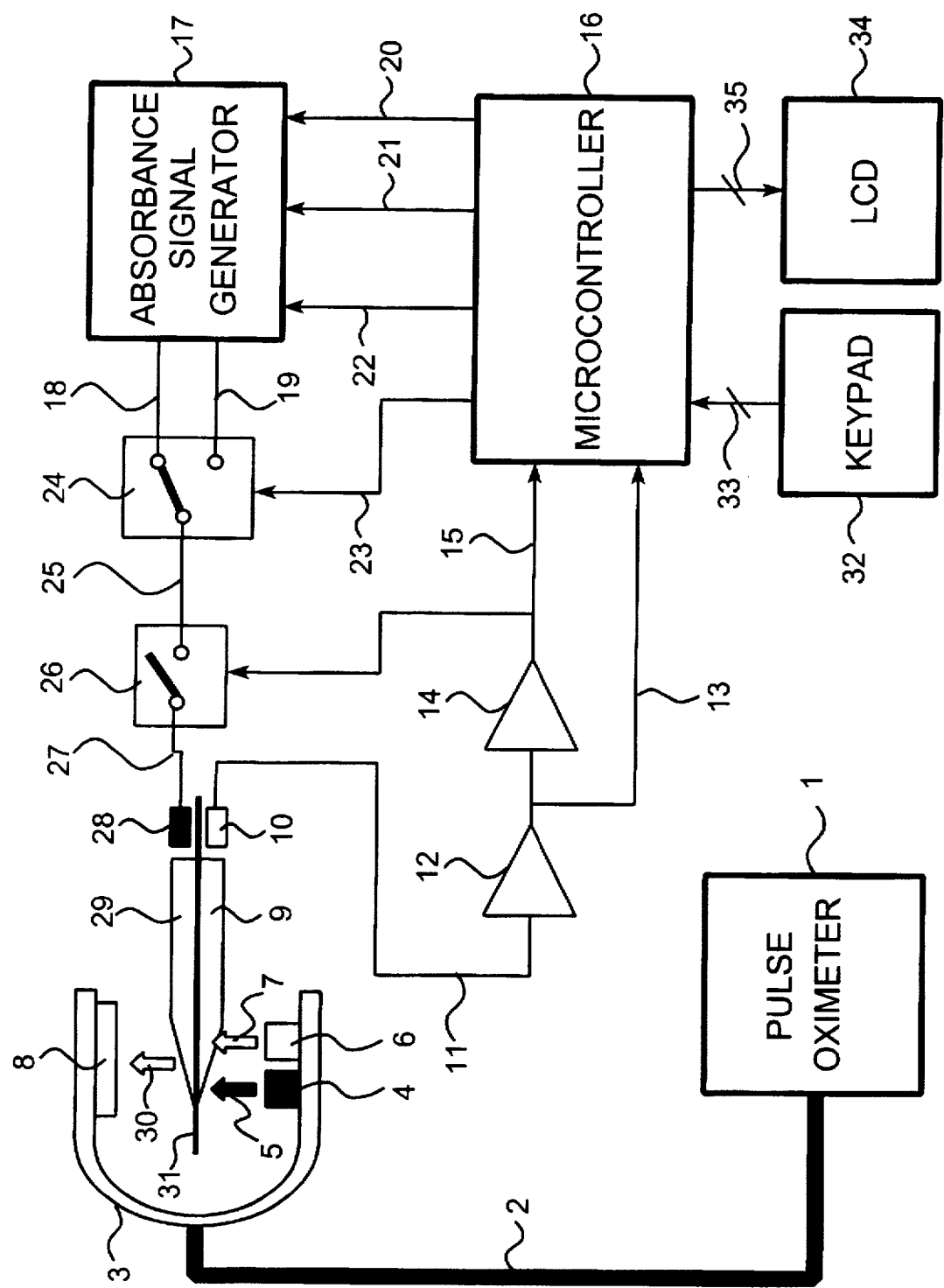
FIG. 1 is a schematic block diagram illustrating a preferred embodiment of the invention for testing a two-wavelength pulsed light oximeter.

Referring to FIG. 1, pulse oximeter 1 connects via cable 2 to transilluminating sensor 3. Sensor 3 includes infrared light emitter 4 which produces infrared light flashes 5 of a predefined intensity and a predefined timing sequence under the control of pulse oximeter 1 via cable 2. Sensor 3 also includes red light emitter 6 which produces red light flashes 7 of a predefined intensity and a predefined timing sequence under the control of pulse oximeter 1 via cable 2. Pulse oximeter 1 activates emitters 4 and 5 periodically and in such a way that only infrared emitter 4 or red emitter 6 produces a light flash at any given time.

Optical detector 8 of sensor 3 converts light flashes to an electrical signal which is conveyed via cable 2 to pulse oximeter 1. In operation, pulse oximeter 1 demultiplexes the electrical signal from detector 8 and internally reconstructs red and infrared absorbance signals representative of the absorbance of an object, which may be a finger or ear lobe, inserted between emitters 4 and 6 and detector 8. In this way, pulse oximeter 1 is able to derive an estimate of the oxygen saturation of blood in a transilluminated object.

The use of sequentially-activated emitters 4 and 6, and the reconstruction of the absorbance signals at red and infrared wavelengths by demultiplexing is the underlying principle by which most commercial pulse oximeters operate today. The following description of the preferred embodiment of the invention will illustrate how the timing and/or amplitude of the light flashes produced by emitters 4 and 6, which are predefined for any given make of pulse oximeter, can be advantageously exploited to test pulse oximeter 1 in combination with sensor 3.

Referring again to FIG. 1, infrared flashes 5 and red flashes 7 are intercepted and conducted by prism 9, which is positioned within sensor 3, to light sensing means 10. Sensing means 10 produces detected light signal 11 which is amplified by signal conditioner 12 to produce electrical pulse signal 13. Pulse signal 13 is further processed by comparator 14 to produce synchronization signal 15. Pulse signal 13, which is an analog signal directly representative of light flashes 5 and 7, is responded to by microcontroller 16. Synchronization signal 15, which is a digital signal representative of light flashes 5 and 7 stripped of amplitude variation, is also responded to by microcontroller 16.

Absorbance signal generator 17 produces infrared absorbance signal 18 and red absorbance signal 19 in response to ratio control signal 20, plethysmogram control signal 21 and baseline control signal 22 produced by microcontroller 16. Analog switch 24 selects either infrared absorbance signal 18 or red absorbance signal 19 depending on the state of wavelength select signal 23 output from microcontroller 16. The output of switch 24 is selected absorbance signal 25 which is conveyed to analog switch 26. Switch 26, under the control of synchronization signal 15, outputs selected and gated absorbance signal 27 to light radiating means 28. Light from radiating means 28 is conducted by prism 29 to the interior of sensor 3, where simulated absorbed light 30 is dispersed from prism 29 over optical detector 8 of sensor 3. In the preferred embodiment, barrier 31 is physically located as schematically illustrated in FIG. 1, separating prism 9 and sensing means 10 from prism 29 and radiating means 28.

The user interface of the preferred embodiment is provided by keypad 32, which conveys user command signals 33 to microcontroller 16, and liquid crystal display (LCD) 34, which receives LCD control signals 35 from microcontroller 16 to display information to the user.

Figure 2:
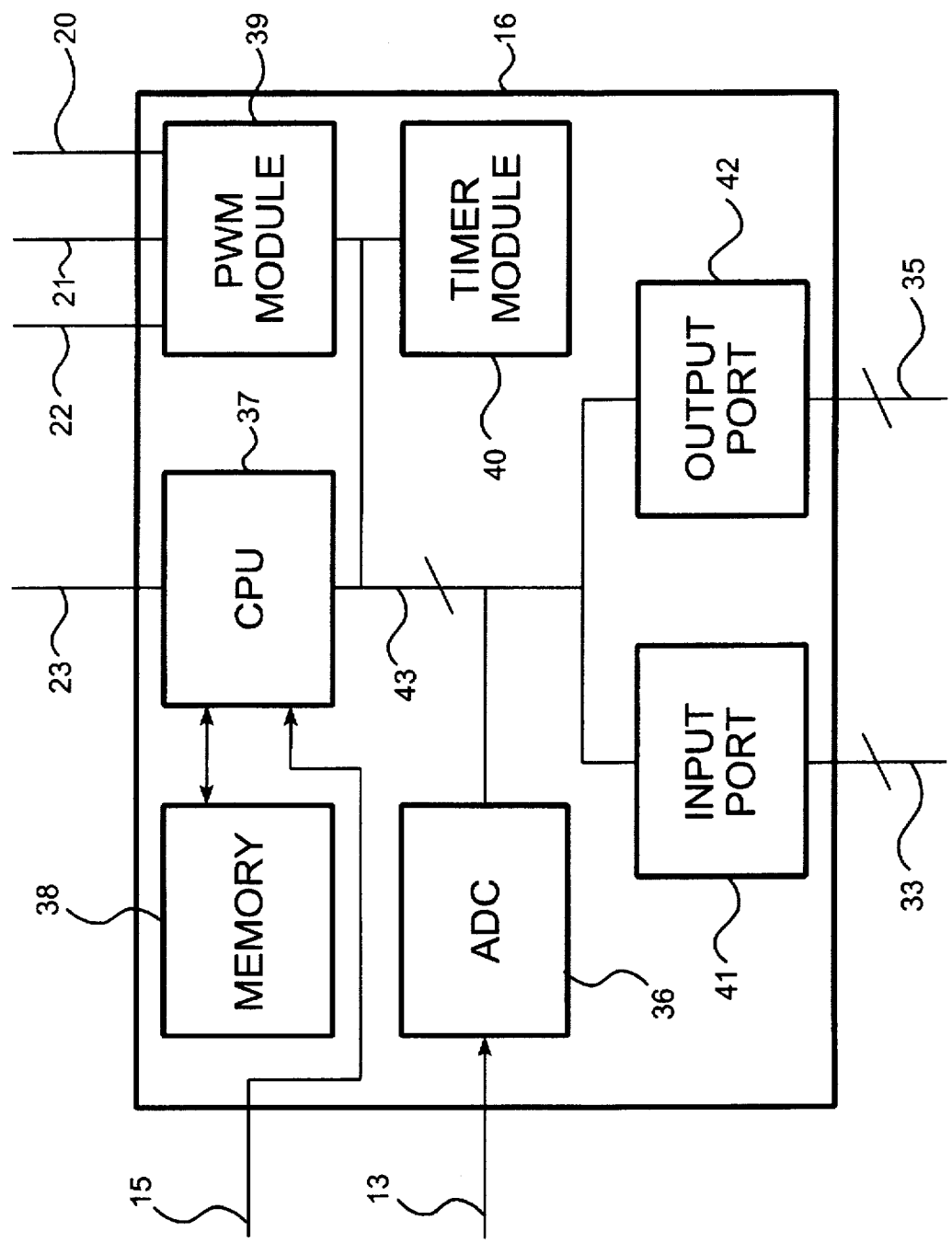
FIG. 2 is a schematic block diagram of the microcontroller of the invention.

FIG. 2 illustrates the hardware modules which comprise microcontroller 16 of FIG. 1. These hardware modules include analog to digital converter (ADC) 36 which converts electrical pulse signal 13 to digital representation; central processing unit (CPU) 37 which executes a sequence of instructions according to the program stored in memory 38; pulse width modulation (PWM) module 39 which is operated by CPU 37 to produce ratio control signal 20, plethysmogram control signal 21, and baseline control signal 22; timer module 40 which facilitates CPU 37 in the timing of events; input port 41 which conveys command signals 33 to CPU 37; and output port 42 which outputs LCD control signals 35 from CPU 37. As shown in FIG. 2, ADC 36, PWM module 39, timer module 40, port 41, and port 42 communicate with CPU 37 via internal buss 43. FIG. 2 also shows that synchronization signal 15 is directly input to CPU 37, and wavelength select signal 23 is output from CPU 37.

Figure 3:
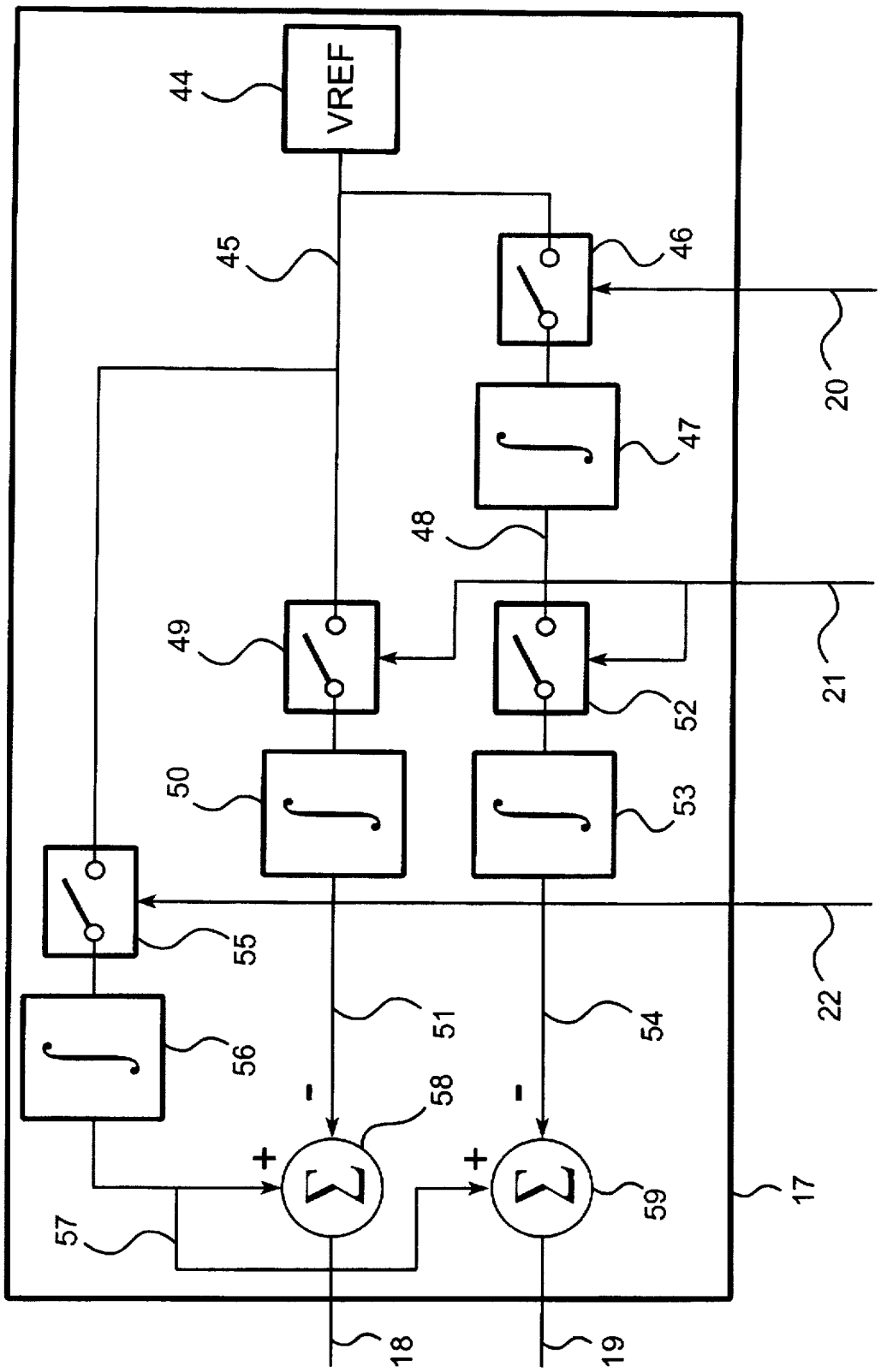
FIG. 3 is a schematic block diagram of the absorbance signal generator of the invention.

FIG. 3 is a block diagram illustrating the components which comprise absorbance signal generator 17 of FIG. 1. Voltage source 44 produces reference voltage 45 which is chopped by analog switch 46 under the control of ratio control signal 20. The output of switch 46 is integrated by third-order integrator 47 to produce reference voltage 48. Reference voltage 45 and reference voltage 48 are chopped by analog switches 49 and 52 respectively under the control of plethysmogram control signal 21. The output of switch 49 is integrated by third-order integrator 50 to produce infrared plethysmogram signal 51, and the output of switch 52 is integrated by third-order integrator 53 to produce red plethysmogram signal 54.

As shown in FIG. 3, reference voltage 45 is also chopped by analog switch 55 under the control of baseline control signal 22. The output of switch 55 is integrated by third-order integrator 56 to produce baseline voltage 57, which is summed with the inverted output of integrator 50 by adder 58 to produce infrared absorbance signal 18. Similarly, baseline voltage 57 is also summed with the inverted output of integrator 53 by adder 59 to produce red absorbance signal 19.

Figure 4A:
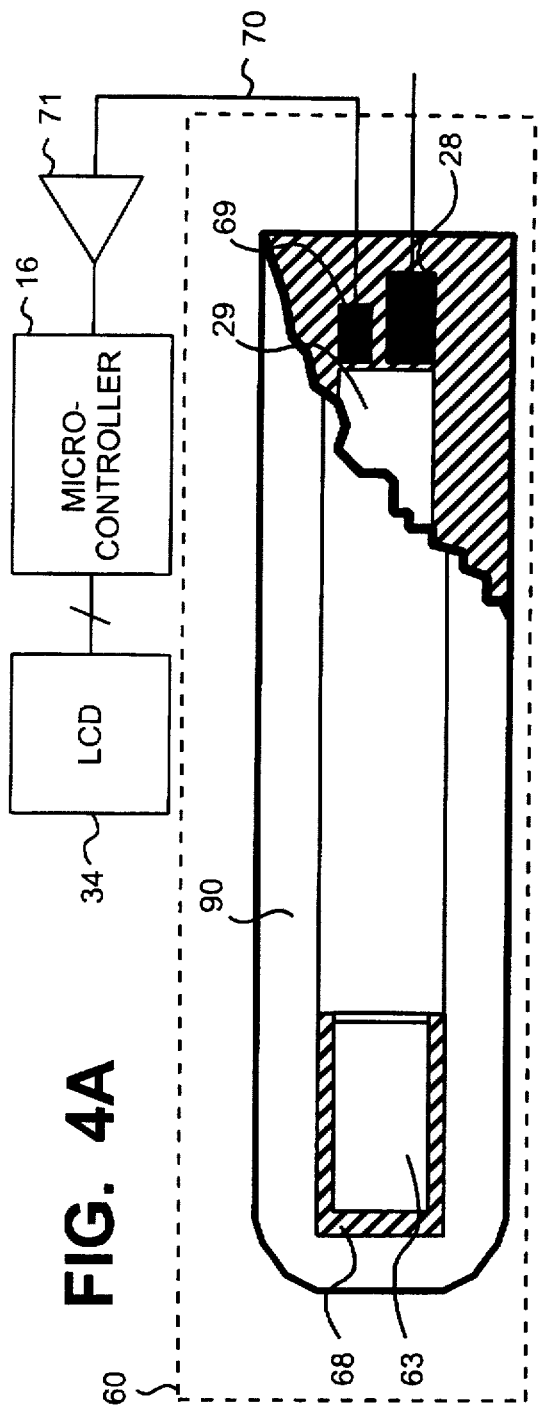
FIGS. 4A and 4B are pictorial representations respectively illustrating plan and cross-sectional views of the probe of the invention.
Figure 4B:
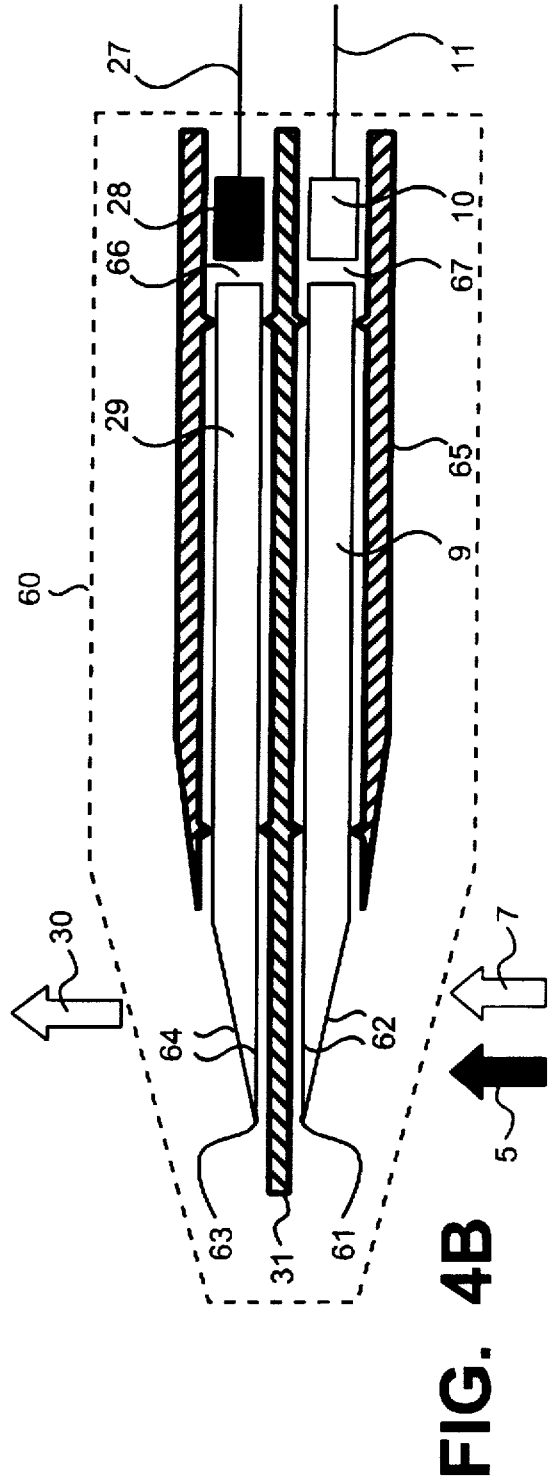

FIGS. 4A and 4B respectively illustrate plan and cross-sectional views of the preferred embodiment of the probe of the invention. Referring to FIGS. 1 and 4B, probe 60 incorporates at one end light sensing means 10 which produces detected light signal 11 representative of light emitted by sensor 3. A long, rectangular prism 9 conducts light from sensor 3 to light sensing means 10. As illustrated by FIG. 4B, prism 9, which has a refractive index greater than air, has one end in the shape of an acute wedge 61. Wedge 61 has a roughened surface 62 to scatter light flashes 5 and 7 impingent upon it from sensor 3, shown in FIG. 1, throughout wedge 61.

Probe 60 also contains light radiating means 28 which produces light to be received by sensor 3 of FIG. 1 in response to gated absorbance signal 27. As shown in FIG. 1, a long rectangular prism 29 conducts light produced by radiating means 28 to optical detector 8 of sensor 3. Referring to FIG. 4B, prism 29, which has a refractive index greater than air, has one end in the shape of an acute wedge 63. Wedge 63 has a roughened surface 64 to disperse simulated absorbed light 30, conducted from radiating means 28, over detector 8 of sensor 3 shown in FIG. 1.

Referring again to FIG. 4B, shell 65 of probe 60 contains prisms 9 and 29, and includes two internal cavities 66 and 67. FIGS. 4A and 4B show that cavities 66 and 67 are open at the distal end 68 of probe 60 to receive wedges 61 and 63 of prisms 9 and 29 respectively. Cavities 66 and 67 are separated by barrier 31 to prevent light transmittance between radiating means 28 and sensing means 10, and between prisms 9 and 29. FIG. 4A also illustrates light sensitive element 69 within cavity 66 located proximal to radiating means 28. Element 69 produces alarm signal 70 which is amplified by signal conditioner 71 and input to microcontroller 16.

A working model of the preferred embodiment of the invention can be assembled according to FIGS. 1, 2, 3 and 4 by persons skilled in the art using the following components: light sensing means 10 can be a SFH206K supplied by Siemens Components Inc. of Iselin N.J.; light radiating means 28 can be a OP268FA and light sensitive element 69 can be a OP508FA, both manufactured by Optek Technology of Carrollton Tex.; analog switches 24, 26, 46, 49, 52 and 55 may each be MC14053BCP manufactured by Motorola Semiconductor Products Inc. of Austin TX; comparator 14 can be a LM393N and voltage source 44 can be a LP2950-CZ5, both manufactured by National Semiconductor Corp. of Santa Clara Calif.; microcontroller 16 can be a HD6475328CP10 supplied by Hitachi America Ltd. of Brisbane Calif.; LCD 34 can be a AND501, supplied by AND, W. J. Purdy Co. of Burlingame Calif.; and signal conditioners 12 and 71, and integrators 47, 50, 53 and 56 may all be assembled using operational amplifiers type TL062ACP manufactured by Texas Instruments Inc. of Dallas Tex.

In the working model of the preferred embodiment, prisms 9 and 29 are machined from 3.3 inches of clear acrylic rectangular extrusion having cross-sectional dimensions of 0.125 inches by 0.375 inches. Roughened surfaces 62 and 64 of wedges 61 and 63 respectively may be created by first polishing prisms 9 and 29, and then hand sanding or sand blasting wedges 61 and 63. Shell 65 is cast from RC-884FR urethane manufactured by BJB Enterprises of Garden Grove Calif. To achieve the high degree of optical opacity required by shell 65, the urethane is pigmented with #6607 black pigment, also manufactured by BJB Enterprises of Garden Grove Calif. In the working model of the preferred embodiment, shell 65 is cast in a shape substantially equivalent to the shape of a human digit as shown in FIGS. 4A and 4B.

Referring to FIGS. 1 and 2, the apparatus for testing pulse oximeter 1 operates generally in the following manner. The user applies sensor 3 to the apparatus as illustrated schematically in FIG. 1. Light flashes 5 and 7 produced by sensor 3 illuminate prism 9 and are conveyed by total internal reflection to light sensing means 10. Light sensing means 10 produces detected light signal 11 which is amplified by signal conditioner 12 to produce electrical pulse signal 13 representative of light flashes 5 and 7 emitted by sensor 3 of pulse oximeter 1, each light flash emitted having a predefined wavelength of primarily red or primarily infrared light. Referring to FIG. 2, electrical pulse signal 13 is input to ADC 36 of microcontroller 16 for conversion to digital representation. Electrical pulse signal 13 is also converted to a logic signal by comparator 14, which outputs synchronization signal 15 directly to CPU 37 of microcontroller 16.

Microcontroller 16 and analog switch 24 embody the selecting means of the invention. Triggered by synchronization signal 15, microcontroller 16 responds to one or more features of electrical pulse signal 13 to determine the wavelength of each light flash 5 or 7 produced by sensor 3, and accordingly outputs wavelength select signal 23 to switch 24 to select signal 18 or signal 19 to produce selected absorbance signal 25. The features of electrical pulse signal 13 responded to by microcontroller 16, either singly or in combination, include the time interval between, the duration of, or the amplitude of individual pulses which comprise electrical pulse signal 13. In this way, microcontroller 16 is advantageously able to discriminate the respective wavelengths of light flashes 5 and 7 without resorting to optical filtering means. Examples of how microcontroller 16 discriminates infrared light flashes 5 from red light flashes 7 based on the features of pulse signal 13 will be presented shortly.

For each pulse of signal 13 which microcontroller 16 determines to correspond to an infrared light flash 5, CPU 37 sets wavelength select signal 23 to a logical zero state so that analog switch 24 selects infrared absorbance signal 18. For each pulse of signal 13 which microcontroller 16 determines to correspond to a red light flash 7, microcontroller 16 sets wavelength select signal 23 to a logical one state so that analog switch 24 selects red absorbance signal 19. Microcontroller 16 and switch 24 thereby produce selected absorbance signal 25.

Selected absorbance signal 25 is gated by analog switch 26 under the control of synchronization signal 15 to produce selected and gated absorbance signal 27. Light radiating means 28, responsive to selected and gated absorbance signal 27, is thereby activated only when infrared light flash 5 or red light flash 7 is detected by light sensing means 10. Light from radiating means 28, conducted by prism 29 to sensor 3, thereby produces flashes of simulated absorbed light 30 which are synchronized to light flashes 5 and 7, and so will be correctly demultiplexed and reconstructed by pulse oximeter 1 once received by optical detector 8.

Absorbance signal generator 17 produces a plurality of absorbance signals 18 and 19 representative of the optical absorbance of an anatomical part, such as the index finger or the ear lobe of a patient, at the wavelength of each light flash 5 or 7. Absorbance signal generator 17, illustrated in FIG. 3, operates under the control of PWM module 39 of microcontroller 16 shown in FIG. 2 as follows.

Referring to FIGS. 2 and 3, ratio control signal 20 from PWM model 39 is a pulse width modulated logic signal which operates analog switch 46. The duty cycle of ratio control signal 20 represents the ratio of the red light absorbance of an anatomical part, such as a finger, to the infrared light absorbance of such a finger. Switch 46 chops d.c. reference voltage 45 under control of signal 20 to produce, after filtering by integrator 47, d.c. reference voltage 48. In the preferred embodiment, integrator 47 is configured to have a gain of two, and the duty cycle of signal 20 from PWM module 39 may be varied under the control of CPU 37 so that reference voltage 45 is multiplied by a factor ranging from 0.2 to 1.8 to produce reference voltage 48.

Plethysmogram control signal 21, produced by PWM module 39 under the control of CPU 37, operates analog switches 49 and 52. The duty cycle of control signal 21 represents the time-varying component of the absorbance signal, known as the "plethysmogram", which would be produced by a transilluminated anatomical part such as a finger. Plethysmogram control signal 21 activates switch 49 which chops reference voltage 45. The output of switch 49 is filtered by integrator 50 to produce infrared plethysmogram signal 51. Thus absorbance signal generator 17 of FIG. 3 multiplies reference voltage 45 by control signal 21 to produce infrared plethysmogram signal 51 of peak amplitude equal to reference voltage 45. Similarly, reference voltage 48 is multiplied by control signal 21 via switch 52 and integrator 53 to produce red plethysmogram signal 54, which has peak amplitude equal to reference voltage 48. Since reference voltage 48 is derived from reference voltage 45 by multiplication with ratio control signal 20 as described above, CPU 37 via PWM module 39 can control the ratio of the amplitudes of red signal 54 to infrared signal 51 over a range of 0.2 to 1.8.

Absorbance signal generator 17 synthesizes d.c. baseline signal 57 by multiplying baseline control signal 22, produced by PWM module 39 under the control of CPU 37, with d.c. reference voltage 45 via analog switch 55 and integrator 56. CPU 37 sets the duty cycle of control signal 22 to achieve a preset amplitude for baseline voltage 57. Adder 58 sums baseline voltage 57 with the inverted version of infrared plethysmogram signal 51 to produce infrared absorbance signal 18. Adder 58 is designed so that baseline 57 and plethysmogram 51 are mixed in a ratio of twenty to one, thereby simulating the large static component representative of tissue and venous blood in an anatomical part, such as a finger, and the smaller time-varying component representative of arterial blood flow through the anatomical part. Similarly, adder 59 sums baseline voltage 57 with the inverted version of red plethysmogram signal 54 to produce red absorbance signal 19. Like adder 58, adder 59 is designed so that baseline 57 and plethysmogram 54 are mixed in a ratio of twenty to one.

FIGS. 5A, 5B, 5C and 5D illustrate examples of waveforms produced by absorbance signal generator 17. FIG. 5A shows two cycles of infrared plethysmogram 51 which has peak amplitude equal to reference voltage 45. Each cycle of plethysmogram 51 shown in FIG. 5A is repeated periodically under the control of CPU 37 via PWM module 39. FIG. 5B shows two cycles of red plethysmogram 54 which has peak amplitude equal to reference voltage 48, derived from reference voltage 45 as described above.

As suggested in FIGS. 5A and 5B, the amplitude of red plethysmogram 54 is approximately one-half the amplitude of infrared plethysmogram 51 for this particular example. FIG. 5C illustrates the result of adder 58 summing the attenuated and inverted version of signal 51 shown in FIG. 5A with baseline signal 57 to produce infrared absorbance signal 18, and FIG. 5D illustrates the result of adder 59 summing the attenuated and inverted version of signal 54 shown in FIG. 5B with baseline signal 57 to produce red absorbance signal 19.

Referring to FIGS. 2 and 3, CPU 37 executes a sequence of instructions in memory 38 which causes absorbance signals 18 and 19 to be continuously produced by absorbance signal generator 17 in the manner just described. Thereby, each absorbance signal 18 and 19 of the plurality generated by absorbance signal generator 17 comprises a static component representative of tissue and venous blood in an anatomical part, and a time-varying component representative of arterial blood flow through the anatomical part. In the preferred embodiment, the waveshape of plethysmogram signals 51 and 54, illustrated in FIGS. 5A and 5B respectively and conveyed by the duty cycle of plethysmogram control signal 21, is defined by a look-up table of 32 duty cycles stored in memory 38 which is read by CPU 37 and conveyed to PWM module 39 in response to a periodic interrupt generated by timer module 40. It should be obvious to those skilled in the art that such a look-up table may contain any number of duty cycles ordered in any sequence to define an arbitrary waveform, or even a nonvarying d.c. level. Additionally, it should be obvious to those skilled in the art that memory 38 may also contain any number of such waveform look-up tables, which, via keypad 32, the user may select for output by absorbance signal generator 17.

Referring now to FIG. 1, microcontroller 16 operates switch 24 to select the absorbance signal 18 in response to infrared light flashes 5, or absorbance signal 19 in response to red light flashes 7 as described previously. Selected absorbance signal 25 so produced by switch 24 is converted to light flashes by switch 26 and light radiating means 28 to produce simulated absorbed light 30, simulating the effect of an anatomical part, such as a finger, on light flashes 5 and 7 emitted by pulse oximeter 1. Pulse oximeter 1 demultiplexes simulated absorbed light 30 conveyed via detector 8 and cable 2, and internally reconstructs absorbed light signals similar to infrared absorbance signal 18 shown in FIG. 5C and red absorbance signal 19 shown in FIG. 5D. Pulse oximeter 1 derives and displays to the user an oxygen saturation value from a ratio S:

$$S=[AC_R/DC_R]/[AC_{IR}/DC_{IR}]$$

where $AC_R$ and $DC_R$ are respectively representative of the amplitude of the time-varying component and the baseline of red absorbance signal 19 shown in FIG. 5D; and $AC_{IR}$ and $DC_{IR}$ are respectively representative of the amplitude of the time-varying component and baseline of infrared absorbance signal 18 shown in FIG. 5C. As illustrated in FIG. 3 and indicated in FIGS. 5A, 5B, 5C and 5D, absorbance signal generator 17 uses one baseline voltage 57 and the same plethysmogram waveshape shown in FIGS. 5A and 5B in producing absorbance signals 18 and 19, and so ratio S obtained by pulse oximeter 1 is completely determined by the ratio of reference voltage 48 to reference voltage 45, and thus by the duty cycle of ratio control signal 20.

By means of keypad 32, the user may command microcontroller 16 to set the duty cycle of ratio control signal 20 to a preselected value, and thereby set ratio S obtained by pulse oximeter 1 to produce a desired oxygen saturation indication. That is, by setting the duty cycle of ratio control signal 20 to a preselected value, the amplitude of each absorbance signal 18 and 19 of the plurality is thereby preselected to produce a predefined oxygen saturation indication on pulse oximeter 1. This feature can be advantageously applied as follows.

Consider the case where pulse oximeter 1 and sensor 3 are known to be calibrated and in good working order, and so provide a suitable reference for comparison with pulse oximeters and sensors of unknown calibration or operating condition. By varying the duty cycle of ratio control signal 20 via keypad 32 and observing the saturations indicated by reference pulse oximeter 1, the user may calibrate the apparatus of FIG. 1 to reference pulse oximeter 1 and reference sensor 3. Thus, the user may derive a table of duty cycles of ratio control signal 20 corresponding to predefined oxygen saturation indications on pulse oximeter 1. This table of duty cycles may then be stored in memory 38 as a set of preselected duty cycles, representing preselected amplitudes for each absorbance signal 18 and 19.

Now consider the use of the apparatus of FIG. 1 in testing a pulse oximeter and sensor of the same make and model type as reference pulse oximeter 1 and reference sensor 3, but of unknown calibration and working condition. The user, by means of keypad 32, may select one of the preselected duty cycles for ratio control signal 20 previously stored in memory 38, thereby producing preselected amplitudes for each absorbance signal 18 and 19. If the pulse oximeter and sensor under test are calibrated and in good working condition, then the saturation indicated by the pulse oximeter being tested will be the same as that displayed by reference pulse oximeter 1 in response to the apparatus of FIG. 1. Thus, by setting the duty cycle of ratio control signal 20 to a preselected value, the amplitude of each absorbance signal 18 and 19 of the plurality is preselected to produce a predefined oxygen saturation indication on the device under test, allowing the user to verify its calibration compared to reference pulse oximeter 1 and reference sensor 3.

To perform additional useful tests, the user may command microcontroller 16 via keypad 32 to alter the rate at which the duty cycle of plethysmogram control signal 21 is varied, thereby changing the frequency of plethysmogram signals 51 and 54 shown in FIGS. 5A and 5B. Such a change in period would thereby change the heart rate displayed by pulse oximeter 1 in beats per minute. The rate at which the duty cycle of signal 21 is varied may be represented as a parameter stored in memory 38 of microcontroller 16, and thus a number of such parameters defining the frequency of plethysmogram signals 51 and 54 may be so stored for selection by the user via keypad 32. Thus, the frequency of the time-varying components 51 and 54 of each absorbance signal 18 and 19 is preselected to produce a predefined heart rate indication on pulse oximeter 1.

Also by means of keypad 32, the user may command microcontroller 16 to increase or reduce the range of duty cycles conveyed by plethysmogram control signal 21 to switches 49 and 52 shown in FIG. 3. This would increase or reduce the amplitude of plethysmogram signals 51 and 54 without influencing the ratio of the amplitudes. In this manner, the user may simulate the effect of increased or reduced arterial blood flow in an anatomical part such as the finger, and observe the result on the oxygen saturation and heart rate displayed by pulse oximeter 1. Similarly, the user may command microcontroller 16 to increase or reduce the duty cycle of baseline control signal 22 via keypad 32. This would increase or decrease the baseline of absorbance signals 18 and 19 without influencing the ratio of absorbance signals 18 and 19. In this manner, the user may simulate the effect of increased or decreased tissue thickness or skin pigment in an anatomical part such as the finger, and observe the result on the oxygen saturation and the heart rate displayed by pulse oximeter 1.

LCD 34 of FIG. 1 is a display device which the user may observe while making such selections as described above via keypad 32. In the preferred embodiment, LCD 34, under the control of microcontroller 16, displays the duty cycle of ratio control signal 20 as a percentage oxygen saturation which the user may compare to the saturation displayed by pulse oximeter 1. LCD 34 also displays the rate of change of the duty cycle of plethysmogram control signal 21 as a heart rate in beats per minute, this value also being comparable to the heart rate display of pulse oximeter 1. LCD 34 may also display an arbitrary indication of tissue perfusion, which is representative of the range of duty cycles in plethysmogram control signal 21. Similarly, LCD 34 may display an arbitrary indication of thickness or skin pigment, which is representative of the duty cycle of baseline control signal 22.

The operation of microcontroller 16, which embodies selecting means responsive to one or more features of electrical pulse signal 13 for selecting one of the plurality of absorbance signals 18 or 19 to produce selected absorbance signal 25, will now be illustrated by way of example for a number of specific models of pulse oximeter 1.

Figure 6:
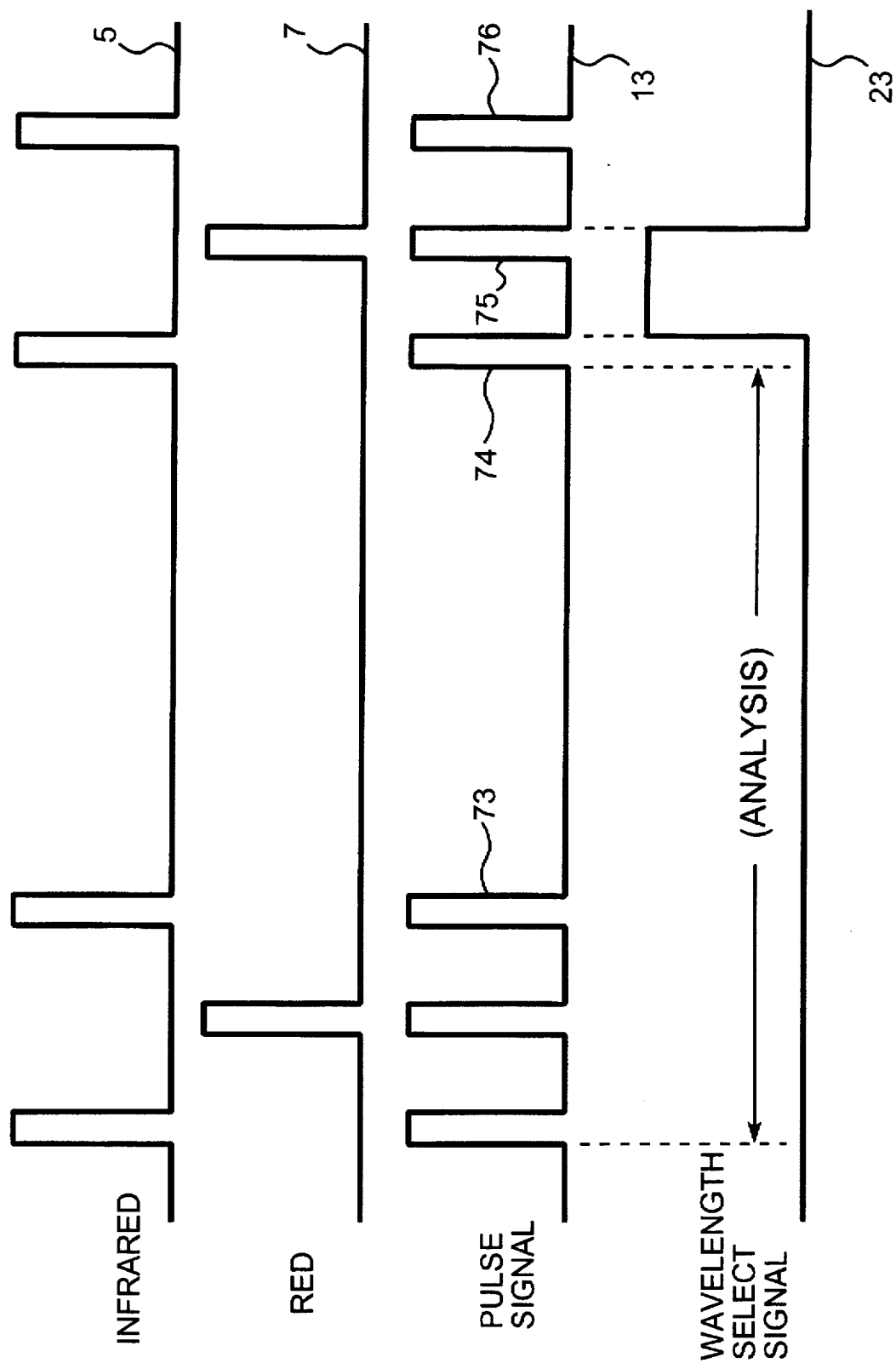
FIG. 6 is a timing diagram illustrating the timing relationships between the light flashes produced by a Nonin model 8600 pulse oximeter and the electrical signals produced by the apparatus of FIG. 1.

The timing diagram of FIG. 6 illustrates the pattern of infrared light flashes 5 and red light flashes 7 produced by a model 8600 pulse oximeter manufactured by Nonin Medical Inc. of Minneapolis Minn. In operating the apparatus of FIG. 1, the user begins by selecting Nonin model 8600 from a list of devices displayed on LCD 34. This causes microcontroller 16 to internally select one algorithm from the sequence of instructions stored in memory 38 of FIG. 2, this algorithm being particular to the Nonin model 8600. When the user applies sensor 3 to prisms 9 and 29, electrical pulse signal 13 and synchronization signal 15 are produced in response to detected light signal 11 from light sensing means 10. Synchronization signal 15 interrupts microcontroller 16 each time Nonin pulse oximeter 1 produces a light flash 5 or 7, causing CPU 37 of FIG. 2 in conjunction with timer module 40 to measure the time interval between interrupts so generated, and thereby the time interval between individual pulses which comprise electrical pulse signal 13.

Referring to FIGS. 1, 2 and 6, microcontroller 16 waits until the time interval between interrupts, as indicated by timer module 40, exceeds a threshold slightly less than the time period shown in FIG. 6 between pulse 73 and pulse 74. During the analysis phase shown in FIG. 6, microcontroller 16 thereby becomes synchronized to the pattern of light flashes 5 and 7 produced by Nonin pulse oximeter 1. Thus at the end of pulse 74, which corresponds to an infrared light flash 5, microcontroller 16 asserts wavelength select signal 23 to select red absorbance signal 19 via switch 24. Selected absorbance signal 25 so produced by microcontroller 16 and switch 24 is then conveyed to detector 8 via switch 26, radiating means 28 and prism 29 in response to pulse 75.

Pulse 75 also causes synchronization signal 15 to interrupt microcontroller 16, which responds by setting wavelength select signal 23 low to select infrared absorbance signal 18 via switch 24. Selected absorbance signal 25 so produced by microcontroller 16 and switch 24 is then conveyed to detector 8 via switch 26, radiating means 28 and prism 29 in response to pulse 76. Once pulse 76 has ended, microcontroller 16 produces wavelength select signal 23 as described for successive groups of three pulses which follow pulses 74, 75 and 76. Thereby, Nonin pulse oximeter 1 receives simulated absorbed light 30 which comprises the absorbance of an anatomical part near the wavelength of red light during the time that red emitter 6 is pulsed, and the absorbance of the anatomical part near the wavelength of infrared light during the time that infrared emitter 4 is pulsed. Thereby, the apparatus simulates the effect of an anatomical part on light flashes 5 and 7 emitted by Nonin pulse oximeter 1.

Figure 7:
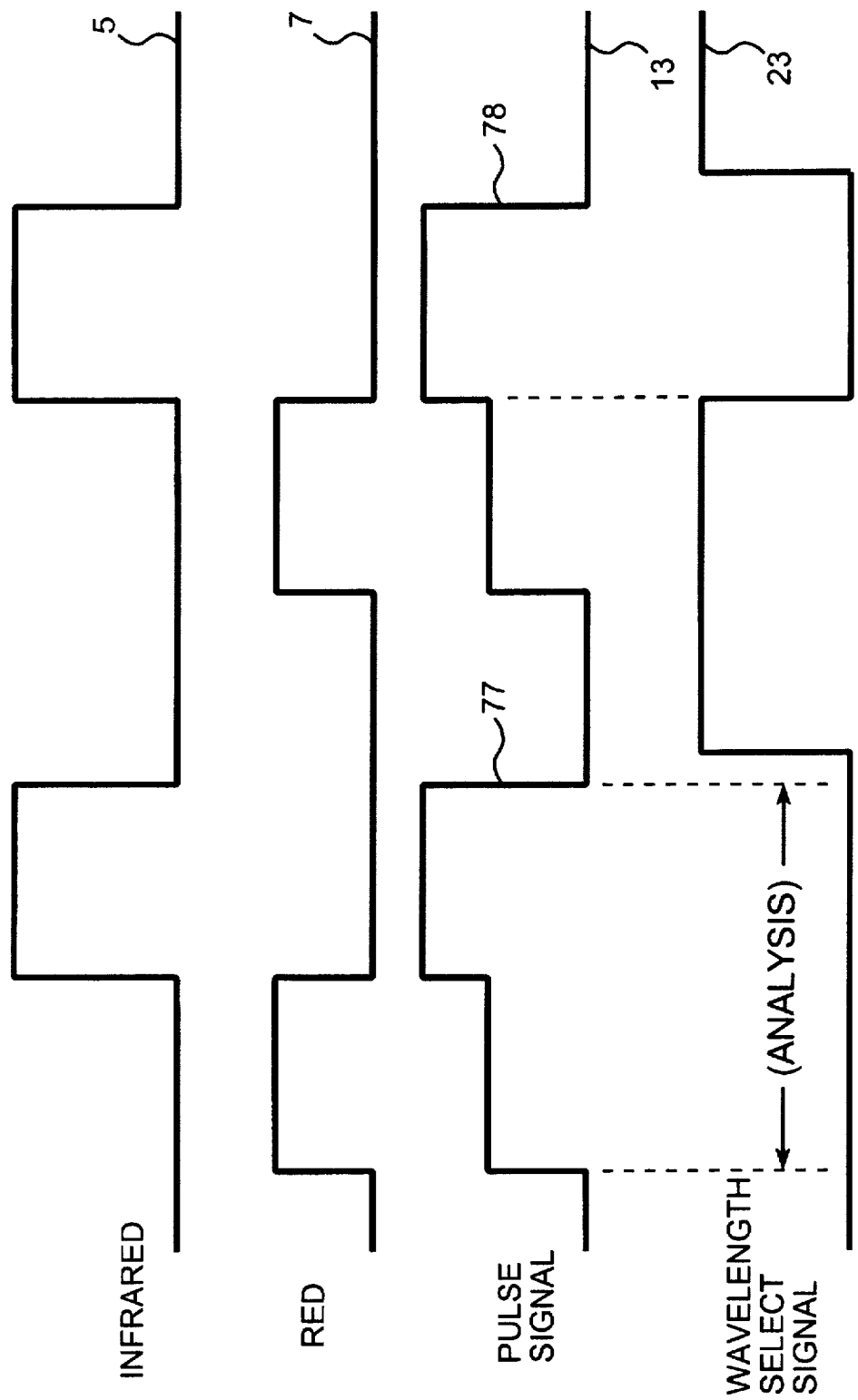
FIG. 7 is a timing diagram illustrating the timing relationships between the light flashes produced by an Ohmeda model 3700 pulse oximeter and the electrical signals produced by the apparatus of FIG. 1.

The timing diagram of FIG. 7 illustrates the pattern of infrared light flashes 5 and red light flashes 7 produced by a model 3700 pulse oximeter manufactured by Ohmeda Inc. of Boulder Colo. In operating the apparatus of FIG. 1, the user begins by selecting Ohmeda model 3700 from a list of devices displayed on LCD 34. This causes microcontroller 16 to internally select one algorithm from the sequence of instructions stored in memory 38 of FIG. 2, this algorithm being particular to the Ohmeda model 3700. When the user applies sensor 3 to prisms 9 and 29, electrical pulse signal 13 and synchronization signal 15 are produced in response to detected light signal 11 from light sensing means 10. Synchronization signal 15 interrupts microcontroller 16 each time a transition occurs in signal 15, causing CPU 37 of FIG. 2 in conjunction with timer module 40 to measure the duration between interrupts so generated, and thereby the duration of individual pulses which comprise electrical pulse signal 13.

Referring to FIGS. 1, 2 and 7, microcontroller 16 determines the duration of pulse 77 using timer module 40, and divides this duration by two to obtain a reference duration which is stored in memory 38. During the analysis phase shown in FIG. 7, microcontroller 16 thereby becomes synchronized to the pattern of light flashes 5 and 7 produced by Ohmeda pulse oximeter 1. Thus at the end of pulse 77, which corresponds to an infrared light flash 5, microcontroller 16 asserts wavelength select signal 23 to select red absorbance signal 19 via switch 24. Selected absorbance signal 25 so produced by microcontroller 16 and switch 24 is then conveyed to detector 8 via switch 26, radiating means 28 and prism 29 in response to the first half of pulse 78.

The rising edge of synchronization signal 15, concurrent with the rising edge of pulse 78 shown in FIG. 7, interrupts microcontroller 16 which responds by loading timer module 40 with the reference duration derived from pulse 77. Timer module 40 counts down and sets wavelength select signal 23 low when a timer count of zero is reached. Thereby, for the latter half of pulse 78, infrared absorbance signal 18 is selected by switch 24. Selected absorbance signal 25 so produced by microcontroller 16 and switch 24 is then conveyed to detector 8 via switch 26, radiating means 28 and prism 29 in response to the latter half of pulse 78. Once pulse 78 has ended, microcontroller 16 produces wavelength select signal 23 as described for successive pulses which follow pulse 78. Thereby, Ohmeda pulse oximeter 1 receives simulated absorbed light 30 which simulates the effect of an anatomical part on light flashes 5 and 7 emitted by Ohmeda pulse oximeter 1.

Figure 8:
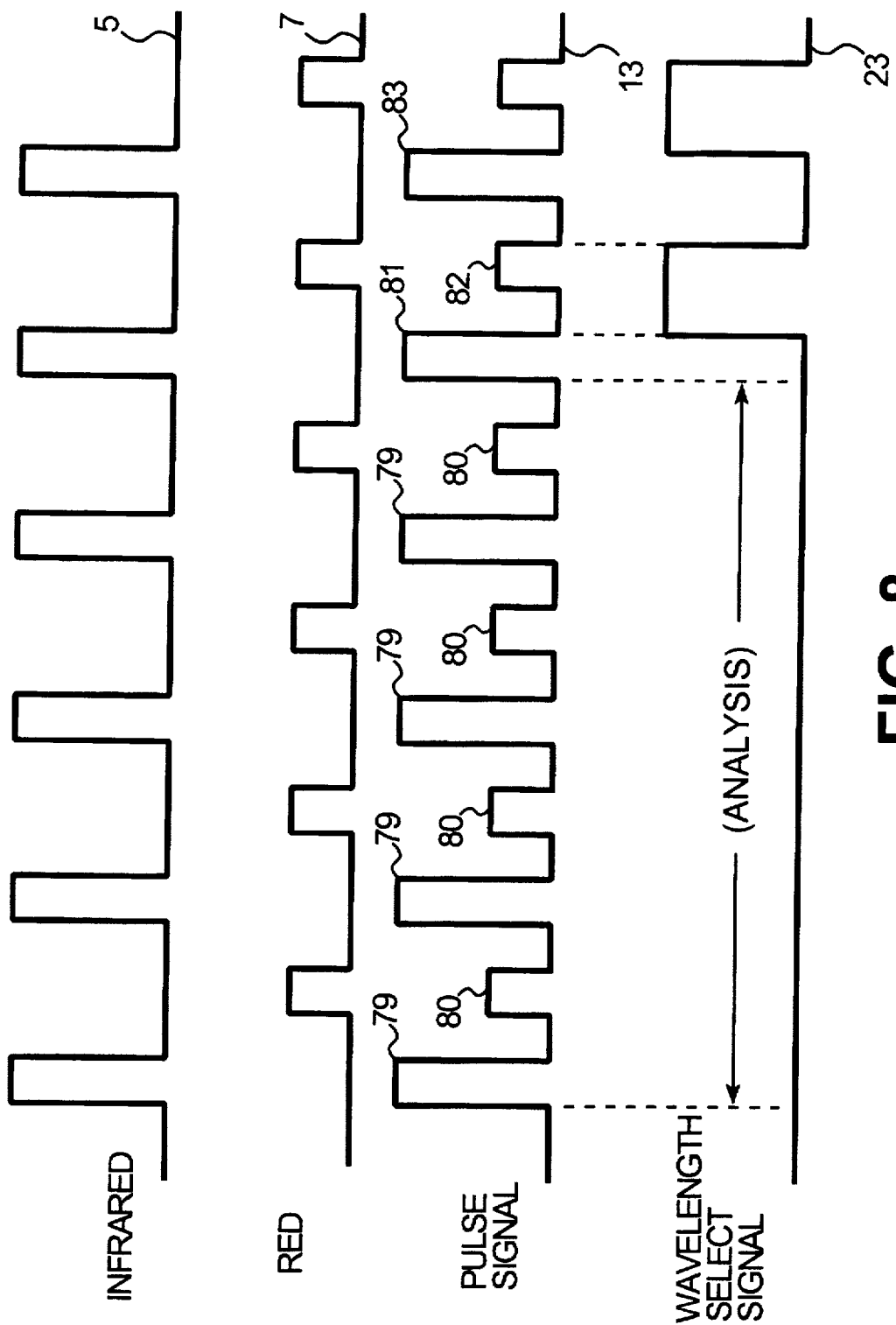
FIG. 8 is a timing diagram illustrating the timing relationships between the light flashes produced by a Nellcor model N-100 pulse oximeter and the electrical signals produced by the apparatus of FIG. 1.

The timing diagram of FIG. 8 illustrates the pattern of infrared light flashes 5 and red light flashes 7 produced by a model N-100 pulse oximeter manufactured by Nellcor Inc. of Hayward Calif. In operating the apparatus of FIG. 1, the user begins by selecting Nellcor model N-100 from a list of devices displayed on LCD 34. This causes microcontroller 16 to internally select one algorithm from the sequence of instructions stored in memory 38 of FIG. 2, this algorithm being particular to the Nellcor model N-100. When the user applies sensor 3 to prisms 9 and 29, electrical pulse signal 13 and synchronization signal 15 are produced in response to detected light signal 11 from light sensing means 10. Synchronization signal 15 interrupts microcontroller 16 each time Nellcor pulse oximeter 1 produces a light flash 5 or 7, causing CPU 37 of FIG. 2 in conjunction with ADC 36 to measure the amplitude of individual pulses which comprise electrical pulse signal 13.

Referring to FIGS. 1, 2 and 8, microcontroller 16 waits until a number of amplitudes has been acquired via ADC 36. During the analysis phase shown in FIG. 8, microcontroller 16 obtains the average amplitude of larger pulses 79 of electrical pulse signal 13 corresponding to infrared light flashes 5, and the average amplitude of smaller pulses 80 corresponding to red light flashes 7. A threshold amplitude is then derived midway between the average amplitude of larger pulses 79 and the average amplitude of smaller pulses 80. When larger pulse 81 occurs, which corresponds to an infrared light flash 5, microcontroller 16 compares the amplitude of pulse 81 to the threshold amplitude and thereby classifies pulse 81 as infrared. Accordingly, microcontroller 16 asserts wavelength select signal 23 at the end of pulse 81 as illustrated by FIG. 7. Microcontroller 16 thereby selects red absorbance signal 19 via switch 24, which is then conveyed to detector 8 via switch 26, radiating means 28 and prism 29 in response to smaller pulse 8 2.

Pulse 82 also causes synchronization signal 15 to interrupt microcontroller 16, which responds by setting wavelength select signal 23 low to select infrared absorbance signal 18 via switch 24. Selected absorbance signal 25 so produced by microcontroller 16 and switch 24 is then conveyed to detector 8 via switch 26, radiating means 28 and prism 29 in response to pulse 83. Once pulse 83 has ended, microcontroller 16 simply toggles wavelength select signal 23 for successive pulses which follow. Thereby, Nellcor pulse oximeter 1 receives simulated absorbed light 30 which simulates the effect of an anatomical part on light flashes 5 and 7 emitted by Nellcor pulse oximeter 1.

The selecting means embodied by microcontroller 16 and switch 24 includes means for producing an alarm signal if the features of electrical pulse signal 13 do not match predefined reference features derived from a priori knowledge of pulse oximeter 1. For example, for the case of the Nellcor N-100, microcontroller 16 produces and alarm signal via LCD 34 if no amplitude difference is found between pulses 79 and 80 of FIG. 8, implying that either infrared emitter 4 or red emitter 6 is not operating. In addition to the amplitudes of pulses 79 and 80 which comprise electrical pulse signal 13, microcontroller 16 may also measure the time interval between pulses 79 and 80 using timer module 40, and produce an alarm signal via LCD 34 if the time interval exceeds a preselected threshold based on the expected inter-pulse interval for the Nellcor N-100. In this case, microprocessor 16 responds to a combination of the time interval between and the amplitude of pulses 79 and 80.

Similarly, microcontroller 16 produces an alarm signal via LCD 34 if the duration of pulse 77 shown in FIG. 7 is less than a preselected threshold based on the expected duration for the Ohmeda 3700. FIG. 7 illustrates the amplitude of red light flash 7 and infrared light flash 5 are different for the Ohmeda 3700, and this information is conveyed by electrical pulse signal 13. Microcontroller 16 may therefore respond to both the amplitude and the duration of pulse 77 of electrical pulse signal 13 and produce an alarm signal if these features do not match predefined reference features derived from a priori knowledge of the Ohmeda 3700. Similarly, referring to FIG. 6, microcontroller 16 may produce an alarm signal via LCD 34 if the time interval between pulses 74, 75 and 76 do not match predefined reference intervals when pulse oximeter 1 is a Nonin model 8600. This alarm signal conveyed by LCD 34, in combination with the oxygen saturation displayed by pulse oximeter 1 in response to the apparatus, advantageously provides a definitive indication that pulse oximeter 1 is functioning normally according to its design.

In the preferred embodiment, the alarm signal produced by microcontroller 16 via LCD 34 may take a number of forms depending on the mismatch between the features of electrical pulse signal 13 and the reference features. For example, the alarm signal may be conveyed as a literal message to the user such as "MISSING INFRARED WAVELENGTH", "MISSING RED/IR WAVELENGTH", "LOW RED INTENSITY" and so on.

Microcontroller 16 may also act to force pulse oximeter 1 to enhance the features of electrical pulse signal 13. For example, if pulse oximeter 1 is a Nellcor model N-100, microcontroller 16 may increase baseline voltage 57 of absorbance signals 18 and 19 so that a greater intensity of simulated absorbed light 30 is emitted by light radiating means 28 through prism 29 to detector 8. Nellcor pulse oximeter 1 responds to the increased intensity of light 30 by reducing the intensity of light flashes 5 and 7 produced by emitters 4 and 6 respectively. However, Nellcor pulse oximeter 1 will tend to reduce the intensity of light flash 7 more than light flash 5 in response to increased intensity of light 30. Thereby, the amplitude difference between pulses 79 and 80 shown in FIG. 8 is increased, increasing the reliability of wavelength discrimination described above.

Similarly, microcontroller 16 may set baseline voltage 57 to a preselected voltage which ensures that Nellcor pulse oximeter 1 will emit different intensities for light flashes 5 and 7 and so produce different amplitudes for pulses 79 and 80. In effect, light radiating means 28 radiates light 30 of a preselected intensity so as to make pulse oximeter 1 emit different amplitudes of light at each wavelength.

In summary, the embodiment shown in FIG. 1 and described above provides useful and novel apparatus for testing a pulsed light oximeter, comprising light sensing means 10 which produces electrical pulse signal 13 representative of light flashes 5 and 7 emitted by oximeter 1, each light flash 5 or 7 emitted having one of two predefined wavelengths, infrared or red respectively; absorbance signal generator 17 for producing absorbance signals 18 and 19 representative of the optical absorbance of an anatomical part, such as the finger of a patient, at the wavelength of each light flash 5 or 7; microcontroller 16 and switch 24 responsive to one or more features of electrical pulse signal 13 for selecting either absorbance signal 18 or absorbance signal 19 to produce selected absorbance signal 25; and light radiating means 28 responsive to selected absorbance signal 25 for radiating light 30 to detector 8 of oximeter 1 to simulate the effect of the anatomical part on light flashes 5 and 7. To produce selected absorbance signal 25, microcontroller 16 responds to features such as the time interval between individual pulses 73 through 76 which comprise electrical pulse signal 13, the duration of individual pulses 77 and 78 which comprise signal 13, or the amplitude of individual pulses 79 and 80 which comprise signal 13, or any of these in combination. The selecting means embodied by microcontroller 16 and switch 24 furthermore includes means for producing an alarm signal via LCD 34 if the features of electrical pulse signal 13 do not match predefined reference features derived from a priori knowledge of oximeter 1.

Figure 9:
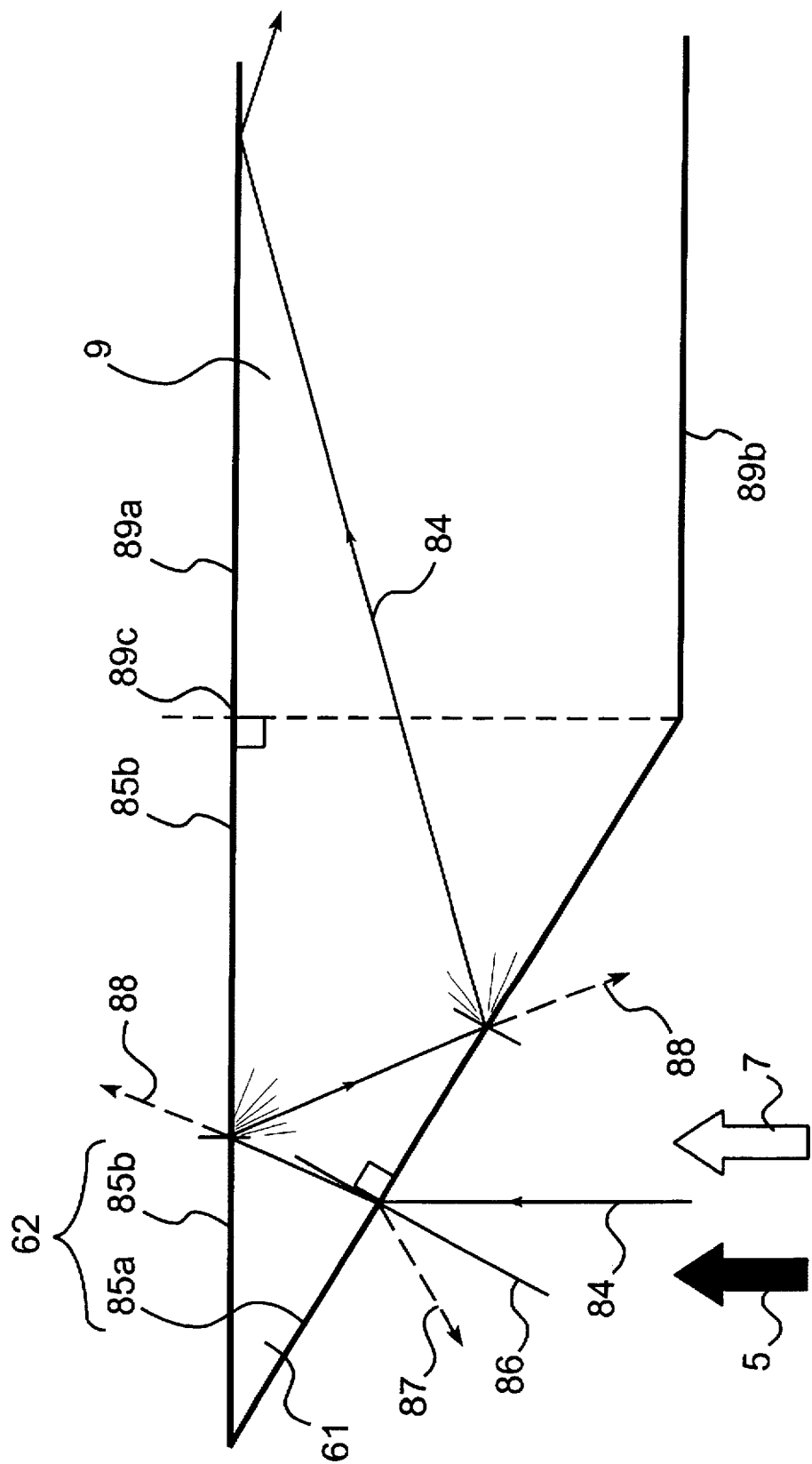
FIG. 9 is a schematic representation of the propagation of light through a prism of the probe of the invention.

FIGS. 4A and 4B are pictorial representations of the preferred embodiment of the probe of the invention, the operation of which will now be explained. Referring to FIG. 4B, light flashes 5 and 7, produced by sensor 3 of FIG. 1, illuminate roughened surface 62 of wedge 61 of prism 9. FIG. 9 illustrates how light flashes 5 and 7 propagate along light path 84 through prism 9. Light flashes 5 and 7 impingent on roughened surface 85a enter prism 9, bending towards normal 86 since the refractive index of prism 9 is greater than that of air. Because of rough surface 85a, there is a backscatter component 87 which does not enter prism 9. Light flashes 5 and 7 continue along path 84 until they are reflected and scattered by roughened surface 85b. Because the angle of incidence of light path 84 does not equal the critical angle for the refractive material of prism 9, there is a loss component 88 which is minimal due to the reflective and scattering properties of roughened surface 85b. Light flashes 5 and 7 continue along path 84, reflecting from roughened surfaces 85a and 85b until path 84 is directed down prism 9. Thereby, roughened surfaces 85a and 85b act to scatter light flashes throughout wedge 61, and minimize losses 88. The length of roughened surface 85b is very nearly equal to the length of roughened surface 85a, and adjoins smooth side 89a of prism 9 at point 89c. Due to the shape of acute wedge 61, light flashes 5 and 7 strike smooth sides 89a and 89b of prism 9 at an oblique angle exceeding the critical angle for the refractive material of prism 9. Thereby, light flashes 5 and 7 are conducted through prism 9 by total internal reflection.

In an alternative embodiment of the invention, surface 85b and sides 89a and 89b are covered with a reflective material such as aluminum foil or mylar. Surface 85a is not covered with reflective material to allow light flashes 5 and 7 to enter prism 9. In this alternative embodiment, losses 88 are somewhat reduced and thus a greater amount of light is propagated through prism 9. However, such reflective surfaces are not essential to the operation of the invention.

Referring now to FIGS. 1 and 4B, the acuteness of wedge 61 allows prism 9 to present a large optical surface 85a for reception of light flashes 5 and 7 from emitters 4 and 6 respectively. Thus, emitters 4 and 6 may be located anywhere within the region projected by surface 85a shown in FIG. 9, and light flashes 5 and 7 will still be propagated through prism 9 to light sensing means 10 of FIG. 4B to produce detected light signal 11.

Referring to FIG. 4B, prism 29 of probe 60 acts in a manner analogous to prism 9, conducting light from radiating means 28 in response to signal 27 via total internal reflection. In the case of prism 29, roughened surface 64 scatters light which enters wedge 63. Simulated absorbed light 30 is thereby dispersed over the surface of detector 8 of sensor 3 shown in FIG. 1. The dispersive effect of roughened surface 64, in addition to the acuteness of wedge 63, means that detector 8 may be located anywhere within the region projected by wedge 63 and simulated light 30 will still be received by detector 8. The low degree of position sensitivity thereby attained by prisms 9 and 29 of probe 60 advantageously reduces the operator skill required to orient sensor 3 on probe 60.

Illustrated in FIGS. 4A and 4B, an essential function of shell 65 of probe 60 is to provide opaque barrier 31 between prisms 9 and 29. Barrier 31, also shown in FIG. 1, prevents optical interference between light sensing means 10 and light radiating means 28, and between prisms 9 and 29. FIG. 4A shows that barrier 31 is of substantially greater extent than would be necessary if isolation of prisms 9 and 29 were the only purpose of barrier 31. An equally essential function of barrier 31 is to prevent light transmittance between light emitters 4 and 6 and optical detector 8 of sensor 3. It has been experimentally determined that repeatability of the apparatus illustrated in FIG. 1 is highly dependent on the ability of barrier 31 to prevent interference between light flashes 5 and 7 and simulated absorbed light 30. Hence, barrier 31 is substantially wider than the width and somewhat longer than the length of prisms 9 and 29 as suggested in FIG. 4A.

As suggested by FIG. 4B, the shape created by shell 65, acute wedges 61 and 63, and barrier 31 is substantially equivalent to the conical shape of a human digit extending from the knuckle to the finger tip. The conical shape so created advantageously achieves a snug fit between probe 60 and a wide range of sensors 3 of the finger-clip, Y-band, or ear-clip style. An additional advantage is provided by planar flange 90 of barrier 31, which, as shown in FIG. 4A, is wider than prisms 9 and 29 and is oriented parallel to prisms 9 and 29. Flange 90 defines the periphery of probe 60 and provides a thin planar surface which finger-clip style sensor 3 may grip onto. Advantageously, flange 90 thereby stabilizes sensors applied to probe 60 and provides an optical seal around the periphery of probe 60 to prevent interference between light flashes 5 and 7 and light 30 emitted by prism 29. As should also be clear from FIG. 4B, the acuteness of wedges 61 and 63 is such that the thickness of probe 60 is not greater than the thickness of a human digit, and is in practise approximately one-half to two-thirds the thickness of a normal adult index finger. Advantageously, the low profile of probe 60 so obtained by the acuteness of wedges 61 and 63 allows a wide range of sensor styles to be applied to probe 60 with reduced disruption of the peripheral optical barrier provided by flange 90.

As shown in FIG. 4A, light sensitive element 69 is located proximal to radiating means 28. Element 69 is used as follows in operation of the apparatus of FIG. 1. Before sensor 3 is applied to probe 60, plethysmogram control signal 21 and baseline control signal 22 are set to a logic low level by microcontroller 16 so that infrared absorbance signal 18 and red absorbance signal 19 are both equal to zero volts. As long as no synchronization signal 15 is received by microcontroller 16, microcontroller 16 continues to observe alarm signal 70 from element 69 as amplified by signal conditioner 71. If sensor 3 is applied to probe 60 with incorrect orientation, for example, if sensor 3 is applied upside down, microcontroller 16 will receive alarm signal 70 from element 69 rather than synchronization signal 15 from light sensing means 10. Consequently, microcontroller 16 informs the user via LCD 34 that sensor 3 is inverted. Advantageously, element 69 produces alarm signal 70 if sensor 3 is applied to probe 60 with incorrect orientation, thereby assisting the operator in applying sensor 3 appropriately.

If sensor 3 is applied to probe 60 in the correct orientation, no alarm signal 70 will be produced by element 69. Instead, microcontroller 16 will receive synchronization signal 15 and will begin to output plethysmogram control signal 20 and 21 so that absorbance signals 18 and 19 similar to those shown in FIGS. 5C and 5D are produced by absorbance signal generator 17. During the analysis period illustrated in FIG. 8, for example, microcontroller 16 displays the amplitude of pulses 79 and 80, measured by ADC 36 and representative of detected light signal 11, and displays an amplitude indication on LCD 34. Advantageously, this assists the operator in optimizing the position of sensor 3 so as to obtain the strongest signal from emitters 4 and 6. Thereby, probe 60 includes the display means of microcontroller 16 in combination with LCD 34 for displaying detected light signal 11 to an operator.

Figure 10:
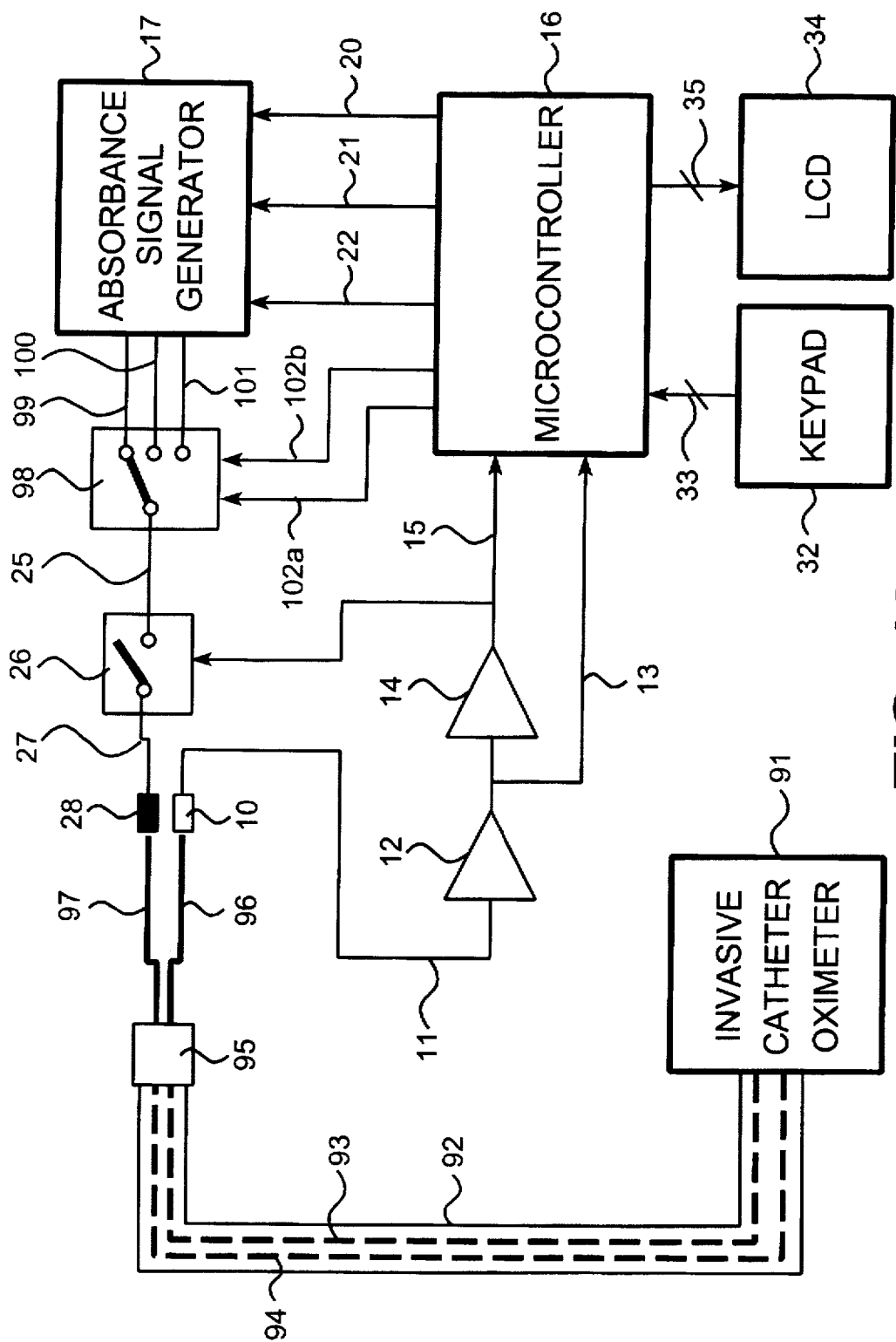
FIG. 10 is a schematic block diagram illustrating a preferred embodiment of the invention for testing an invivo catheter-based oximeter, an example of a three-wavelength pulsed light oximeter.

Although the apparatus of FIGS. 1, 2 and 3 is primarily intended for testing a two-wavelength pulse oximeter 1, the apparatus may be adapted for testing any pulsed light spectrophotometric instrument which emits a multiplicity of arbitrary wavelengths. An example of such an adaptation is illustrated in the block diagram of FIG. 10. Referring to FIG. 10, invasive catheter oximeter 91 is a triple-wavelength pulsed light oximeter, such as the Oximetrix 3 manufactured by Abbott Laboratories of Mountain View Calif. Oximeter 91 provides fibre optic catheter 92 which is normally inserted directly into a major artery of a patient to measure oxygen saturation of the blood in critical care situations. As shown in FIG. 10, internal to catheter 92 are send fibre 93, which normally conveys light flashes from oximeter 91 into a patient's artery, and return fibre 94 which normally conveys light flashes reflected from the patient's blood to oximeter 91. For the case of pulse oximeter 1 shown in FIG. 1, in normal clinical use an anatomical part such as a finger is transilluminated by sensor 3, the light transmitted through the finger being representative of light absorbed by intervening tissue and blood. For the case of catheter oximeter 91 shown in FIG. 10, in normal clinical use the light is reflected from rather than transmitted through the anatomical part, although in this case as well such reflected light is similarly representative of light absorbed by the tissue and blood so illuminated.

Because catheter 92 contains optic fibres 93 and 94, oximeter 91 may be interfaced directly to the testing apparatus shown in FIG. 10 without the need for prisms 9 or 29 which appear in FIG. 1. Consequently, the apparatus of FIG. 10 does not require probe apparatus such as that shown in FIGS. 4A and 4B. Thus, as shown in FIG. 10, send fibre 93 and return fibre 94 connect to fibre optic terminal block 95, which in turn interfaces fibres 93 and 94 to transmit optical fibre 96 and receive optical fibre 97 respectively. Light flashes produced by oximeter 91 are conducted by fibres 93 and 96 directly to light sensing means 10, and simulated absorbed light emitted by light radiating means 28 is similarly conducted by fibres 97 and 94 directly to oximeter 91. For the example of FIG. 10, oximeter 91 emits flashes of light at three predefined wavelengths, and thus absorbance signal generator 17 accordingly produces three absorbance signals 99, 100 and 101 representative of the optical absorbance of blood within an artery at the wavelength of each light flash. Absorbance signals 99, 100 and 101 are selected by three-pole analog switch 98 to produce selected absorbance signal 25 under the control of microcontroller 16, which outputs wavelength select signals 102a and 102b to operate switch 98. Since switch 98 has three positions, two wavelength select signals 102a and 102b are required in this case to binarily identify which of absorbance signals 99, 100 or 101 is to be selected. Analogous to the apparatus of FIG. 1, selected absorbance signal 25 of FIG. 10 so produced by microcontroller 16 and switch 98 is conveyed to receive fibre 97 via analog switch 26 and radiating means 28.

The apparatus of FIG. 10 is analogous to the apparatus of FIG. 1, and hence both operate in a manner equivalent to that previously described for the apparatus of FIG. 1. Consequently, a brief summary of the operation of the three-wavelength apparatus of FIG. 10 follows, the details of such operation being obvious to those skilled in the art given the preceding explanations presented for the two-wavelength cases of FIGS. 6, 7 and 8.

The apparatus of FIG. 10 includes light sensing means 10 which produces electrical pulse signal 13 representative of light flashes emitted by oximeter 91 and conveyed via fibres 93 and 96, each light flash emitted and so conveyed having one of three predefined wavelengths. In response to signals 20, 21 and 22 output by microcontroller 16, absorbance signal generator 17 produces absorbance signals 99, 100 and 101 representative of the optical absorbance of an anatomical part, such as blood within an artery, at the wavelength of each light flash emitted by oximeter 91. Microcontroller 16 and switch 98 respond to one or more features of electrical pulse signal 13, microcontroller 16 and switch 98 thereby selecting either absorbance signal 99, absorbance signal 100 or absorbance signal 101 to produce selected absorbance signal 25. Light radiating means 28 responds to selected absorbance signal 25 and radiates light to oximeter 91 via fibres 97 and 94. To produce selected absorbance signal 25, microcontroller 16 responds to features such as the time interval between, the duration of, or the amplitude of individual pulses which comprise electrical pulse signal 13, or any of these features in combination. Similar to the approach employed for the apparatus of FIG. 1, microcontroller 16 in FIG. 10 outputs control signals 20, 21 and 22 so that the amplitude of each absorbance signal 99, 100 and 101 causes oximeter 91 to produce a predefined oxygen saturation indication.

By far, the most common form of non-invasive oximeter in clinical use today is the pulse oximeter, examples of which include the Nonin, Ohmeda and Nellcor instruments previously mentioned. The use of only two wavelengths in the pulse oximeter, plus the fact that the wavelengths most typically used are broadly separated by almost 300 nanometers, allows some advantageous simplifications to be applied to the apparatus of FIG. 1. The block diagram of FIG. 11 illustrates such an alternative embodiment of apparatus for testing a pulsed light oximeter, in which the oximeter is a pulse oximeter known to emit a predefined wavelength of infrared light.

Figure 11:
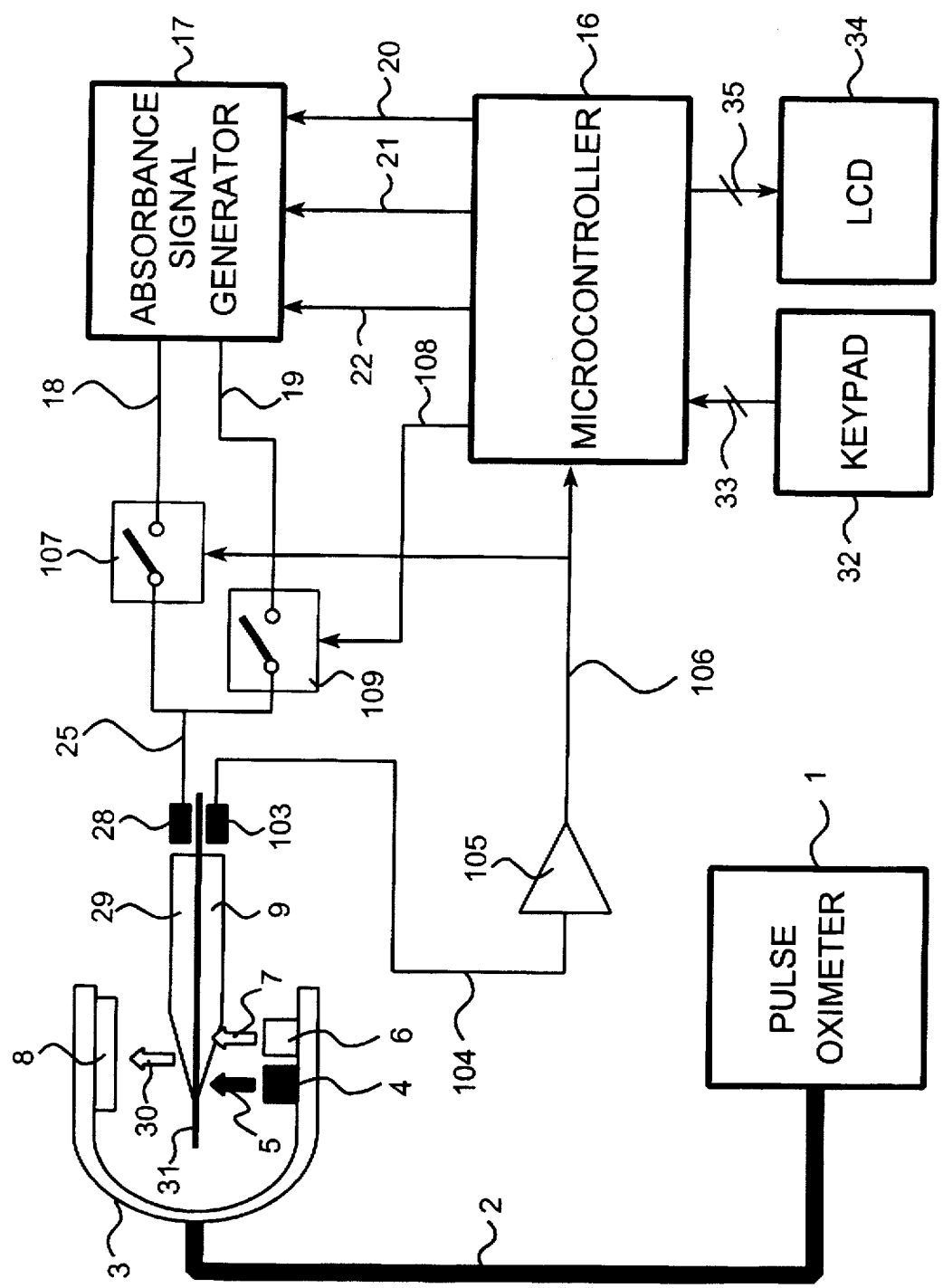
FIG. 11 is a schematic block diagram illustrating a preferred embodiment of the invention for testing a pulsed light oximeter which emits infrared light.

Referring to FIG. 11, light sensing means 103 is similar to light sensing means 10 of FIG. 1, except that sensing means 103 additionally incorporates an optical bandpass filter which accepts infrared light of wavelength approximately ranging from 750 to 1100 nanometers. Sensing means 103 is therefore responsive only infrared light flashes 5 produced by sensor 3, and is unresponsive to red light flashes 7. Sensing means 103 produces synchronization signal 104 which is amplified by signal conditioner 105. Signal conditioner 105 outputs amplified synchronization signal 106 which is responded to by microcontroller 16. With reference to FIG. 2, microcontroller 16 of FIG. 11 similarly incorporates CPU 37, memory 38, timer module 40 and the remaining components 36, 39, 41 and 42 shown in FIG. 2.

Referring to FIG. 11, synchronization signal 106 is also used to actuate analog switch 107, switch 107 being driven by infrared absorbance signal 18 produced by absorbance signal generator 17. Microcontroller 16 outputs regenerated red signal 108 to actuate analog switch 109, switch 109 being driven by red absorbance signal 19 also produced by absorbance signal generator 17. The outputs of switches 107 and 109 are tied together as shown in FIG. 11 to create selected absorbance signal 25 which is used to drive radiating means 28 directly.

In exactly the same manner as previously described for the apparatus of FIGS. 1, 2, and 3, absorbance signal generator 17 of FIG. 11 produces a plurality of absorbance signals 18 and 19 representative of the optical absorbance of an anatomical part, such as a finger or ear lobe, at the wavelength of each light flash 5 or 7. Ratio control signal 20, plethysmogram control signal 21 and baseline control signal 22 output by microcontroller 16 cause signal generator 17 to continuously produce waveforms similar to those which appear in FIG. 5C and 5D respectively. As already described for the apparatus of FIG. 1, the user may operate keypad 32 to vary the frequency, amplitude, and baseline characteristics of infrared absorbance signal 18 and red absorbance signal 19, these characteristics being displayed to the user via LCD 34.

For infrared light flashes 5 produced by emitter 4 of sensor 3, selecting means for selecting absorbance signal 18 to produce selected absorbance signal 25 is provided by analog switch 107. In response to infrared light flashes 5, sensing means 103 and signal conditioner 105 produce synchronization signal 106 which operates analog switch 107 so that infrared absorbance signal 18 is conveyed as selected absorbance signal 25 to radiating means 28. Light from radiating means 28 is conducted by prism 29 to the interior of sensor 3, where simulated absorbed light 30 is dispersed over optical detector 8 of sensor 3. Therefore, in response to each infrared light flash 5, radiating means 28 and prism 29 radiate light 30 to sensor 3 of oximeter 1, simulating the effect of an anatomical part, such as a finger, on infrared light flashes 5 emitted by sensor 3 of oximeter 1.

Sensing means 103 is unresponsive to red light flashes 7 shown in FIG. 11, and so microcontroller 16 and analog switch 109 are included to provide selecting means for selecting red absorbance signal 19 to produce absorbance signal 25. In operation, microcontroller 16 responds to synchronization signal 106 and applies a priori knowledge of the activation sequence of emitters 4 and 6 to produce regenerated red signal 108. The programming of microcontroller 16 is such that synchronization signal 106 causes microcontroller 16 to produce signal 108 at precisely the same instant in time that oximeter 1 activates emitter 6 of sensor 3 to produce red light flash 7. Signal 108 so produced activates analog switch 109, so that red absorbance signal 19 is conveyed as selected absorbance signal 25 to radiating means 28. Light from radiating means 28 is conducted by prism 29 to the interior of sensor 3, where simulated absorbed light 30 is dispersed over optical detector 8 of sensor 3. Therefore, coincident with each red light flash 7, radiating means 28 and prism 29 radiate light 30 to sensor 3 of oximeter 1, simulating the effect of an anatomical part, such as a finger, on red light flashes 7 emitted by sensor 3 of oximeter 1.

Figure 12:
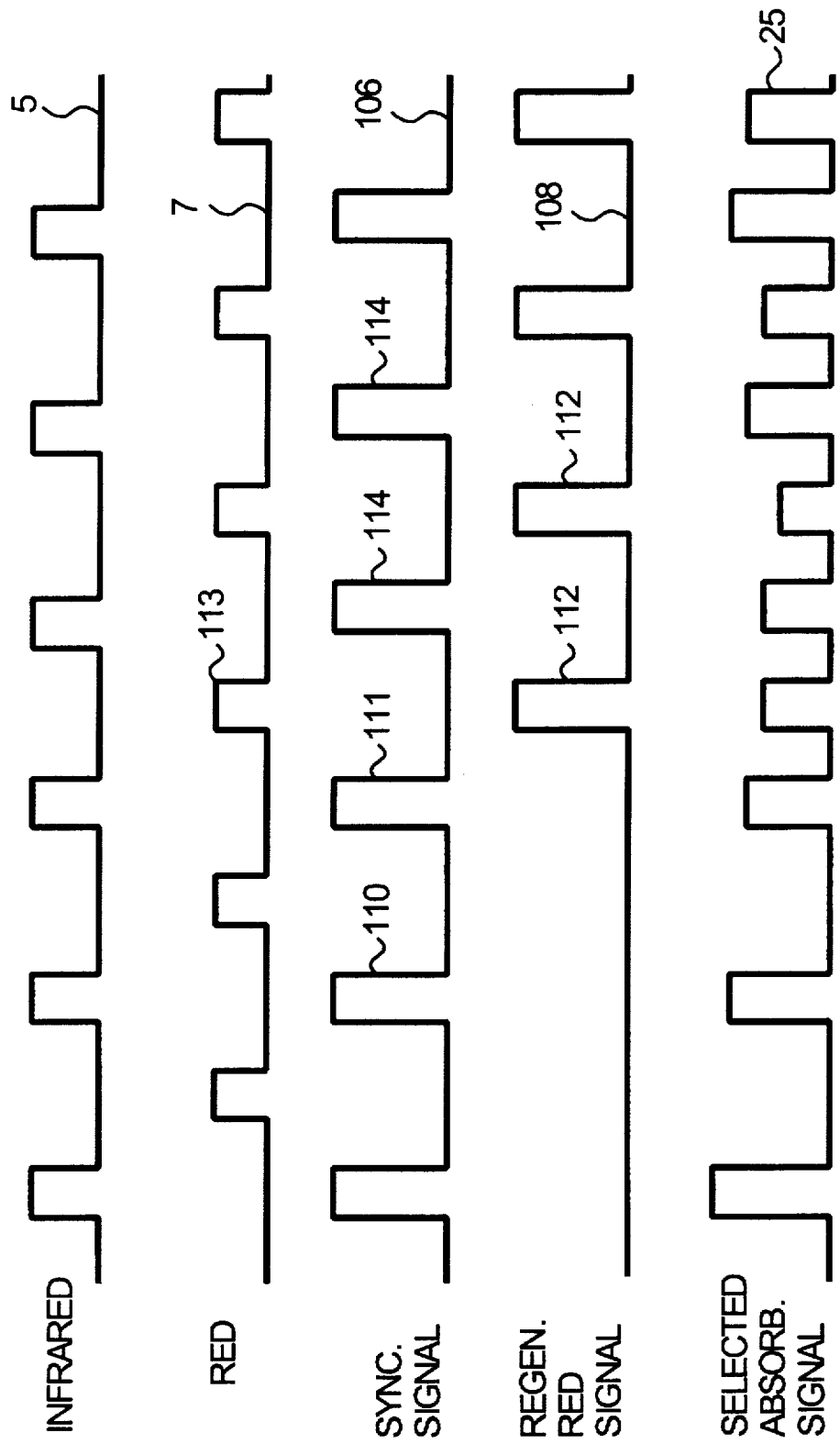
FIG. 12 is a timing diagram illustrating the timing relationships between the light flashes produced by a Nellcor model N-100 pulse oximeter and the electrical signals produced by the apparatus of FIG. 11.

The timing diagram of FIG. 12 illustrates how microcontroller 16 and switches 107 and 109 respond to synchronization signal 106 to produce selected absorbance signal 25 for the case where pulse oximeter 1 is a Nellcor model N-100. In operating the apparatus of FIG. 11, the user begins by selecting the Nellcor model N-100 from a list of devices displayed on LCD 34. This causes microcontroller 16 to internally select one algorithm from the sequence of instructions stored in memory 38 of FIG. 2, this algorithm being particular to the Nellcor model N-100. When the user applies sensor 3 to prisms 9 and 29, synchronization signal 106 is produced by light sensing means 103 and conditioner 105 in response to infrared light flashes 5 as shown in FIG. 12. Synchronization signal 106 interrupts microcontroller 16 each time Nellcor pulse oximeter 1 produces an infrared light flash 5, causing microcontroller 16 to measure the time interval between interrupts so generated, and thereby the time interval between individual pulses 110 and 111 shown in FIG. 12. Microcontroller 16 then derives and stores in memory 38 a reference time interval equal to one-half the time interval measured between pulses 110 and 111. In response to a first interrupt caused by pulse 111, microcontroller 16 resets timer module 40 shown in FIG. 2, and enables a second interrupt to occur when timer module 40 reaches a count equal to the reference duration previously derived. When this second interrupt occurs, microcontroller 16 outputs regenerated red signal pulse 112 as shown in FIG. 12 which is coincident with but otherwise independent of light flash 113 of red light flashes 7. Thereby, red absorbance signal 19 is selected by switch 109 of FIG. 11 and conveyed to Nellcor pulse oximeter 1 by means of radiating means 28, prism 29 and detector 8. As suggested in FIG. 12, subsequent synchronization pulses 114 produce first and second interrupts so that microcontroller 16 periodically outputs regenerated red signal pulses 112 concurrent with red light flashes 7, thereby allowing switches 107 and 109 to select the appropriate absorbance signal 18 or 19 at the correct instant to produce selected absorbance signal 25.

The primary advantage of the apparatus of FIG. 11 over the apparatus of FIG. 1 is that in practise the software algorithms executed by microcontroller 16 for producing regenerated red signal 108 based on the timing of synchronization signal 106 may be less complicated than the software algorithms for producing wavelength select signal 23 based on time interval, duration and amplitude features of electrical pulse signal 13 of FIG. 1. Compared to the apparatus of FIG. 1, however, the apparatus of FIG. 11 has the limitation that only one of the wavelengths emitted by sensor 3 is directly sensed, and so unlike the apparatus of FIG. 1, the apparatus of FIG. 11 is incapable of producing an indication or alarm signal to the user if one or more of the remaining wavelengths normally emitted by sensor 3 are weak or absent. However, for test applications where the apparatus is simply required to produce predefined oxygen saturation and heart rate indications on oximeter 1, the apparatus of FIG. 11 is sufficient.

In summary, the embodiment shown in FIG. 11 and described above provides useful and novel apparatus for testing a pulsed light oximeter, comprising light sensing means 103 which produces synchronization signal 106 representative of light flashes 5 emitted at one of the predefined wavelengths, namely infrared; absorbance signal generator 17 for producing a plurality of absorbance signals 18 and 19 representative of the absorbance of an anatomical part, such as the finger of a patient, at the wavelength of each light flash 5 or 7; microcontroller 16 with switch 109, and switch 107, responsive to synchronization signal 106 for selecting one of absorbance signals 19 or 18 respectively to produce selected absorbance signal 25; and light radiating means 28 responsive to selected absorbance signal 25 for radiating light 30 to detector 8 of oximeter 1 to simulate the effect of the anatomical part on light flashes 5 and 7.

For use with pulse oximeters 1 shown in FIGS. 1 and 11, sensor 3 most commonly incorporates red and infrared light emitting diodes as red emitting element 6 and infrared emitting element 4, these light emitting diodes being activated by electrical drive signals produced by pulse oximeter 1 and conveyed by cable 2 to sensor 3. Another feature common to most pulse oximeters 1 is a connector interface which allows sensor 3 to be detached from pulse oximeter 1 and exchanged with another sensor of the same or different style. These design features common to most pulse oximeters 1 may be advantageously exploited to simplify the apparatus of FIG. 1, and thereby implement apparatus for testing a pulsed light oximeter incorporating light emitting devices activated by electrical drive signals, as schematically illustrated in the block diagram of FIG. 13.

Figure 13:
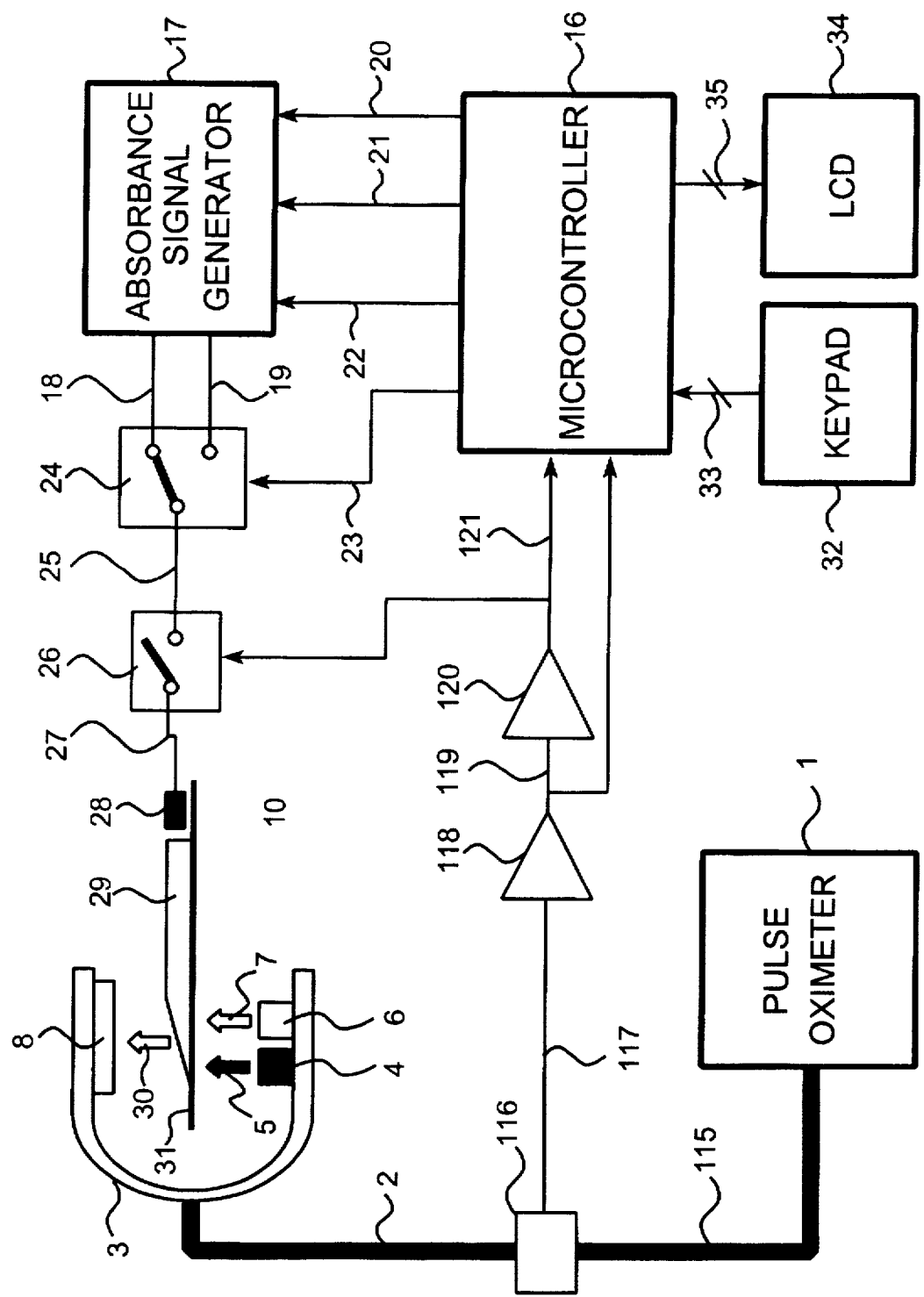
FIG. 13 is a schematic block diagram illustrating an embodiment of the invention for testing a pulsed light oximeter, the oximeter incorporating light emitting diodes which are activated by electrical drive signals.

Referring to FIG. 13, cable 2, which would normally connect directly to pulse oximeter 1 as previously described, connects instead to signal tapping interface 116. Signal tapping interface 116 connects via adaptor cable 115 to pulse oximeter 1 such that continuity is maintained for all required electrical connections between sensor 3 and pulse oximeter 1, and furthermore such that electrical signals which pass between oximeter 1 and sensor 3 via interface 116 are not loaded or otherwise degraded. Within interface 116, electrical drive signal 117 is tapped from the connection by which pulse oximeter 1 activates emitters 4 and 6 of sensor 3 via cable 2. Electrical drive signal 117 is amplified by signal conditioner 118 to produce amplified drive signal 119 to which microcontroller 16 responds. Drive signal 119 is further processed by rectifying comparator 120 to produce synchronization signal 121, a logical signal which assumes a true state when pulse oximeter 1 outputs a current to emitter 4 or 6 via cable 2, and assumes a false state otherwise. Synchronization signal 121 also operates analog switch 26 which, identical to switch 26 of FIG. 1, produces selected and gated absorbance signal 27 from selected absorbance signal 25.

In test situations where it may be disadvantageous or impossible to break the direct connection between sensor 3 and oximeter 1, a coil of wire may alternatively be used as a current probe to inductively detect electrical drive signal 117. Advantageously, such a coil could be easily applied over or proximal to cable 2 without having to insert signal tapping interface 116 between oximeter 1 and sensor 3.

In exactly the same manner as previously described for the apparatus of FIGS. 1, 2, and 3, absorbance signal generator 17 of FIG. 13 produces a plurality of absorbance signals 18 and 19 representative of the optical absorbance of an anatomical part, such as a finger or ear lobe, at the wavelength of each light flash 5 or 7. Ratio control signal 20, plethysmogram control signal 21 and baseline control signal 22 output by microcontroller 16 cause signal generator 17 to continuously produce waveforms similar to those which appear in FIG. 5C and 5D respectively. As already described for the apparatus of FIG. 1, the user may operate keypad 32 to vary the frequency, amplitude, and baseline characteristics of infrared absorbance signal 18 and red absorbance signal 19, these characteristics being displayed to the user via LCD 34.

Similar to the apparatus of FIG. 1, the selecting means of FIG. 13 for selecting signal 18 or 19 to produce signal 25 is provided by microcontroller 16 and analog switch 24, which as in FIG. 1 responds to wavelength select signal 23 produced by microcontroller 16. The apparatus of FIG. 13 differs from the apparatus of FIG. 1 in that microcontroller 16 responds to drive signal 119, which provides an easily-interpreted indication of when oximeter 1 activates emitter 4 to produce an infrared light flash 5, and alternately when oximeter 1 activates emitter 6 to produce a red light flash 7.

Figure 14:
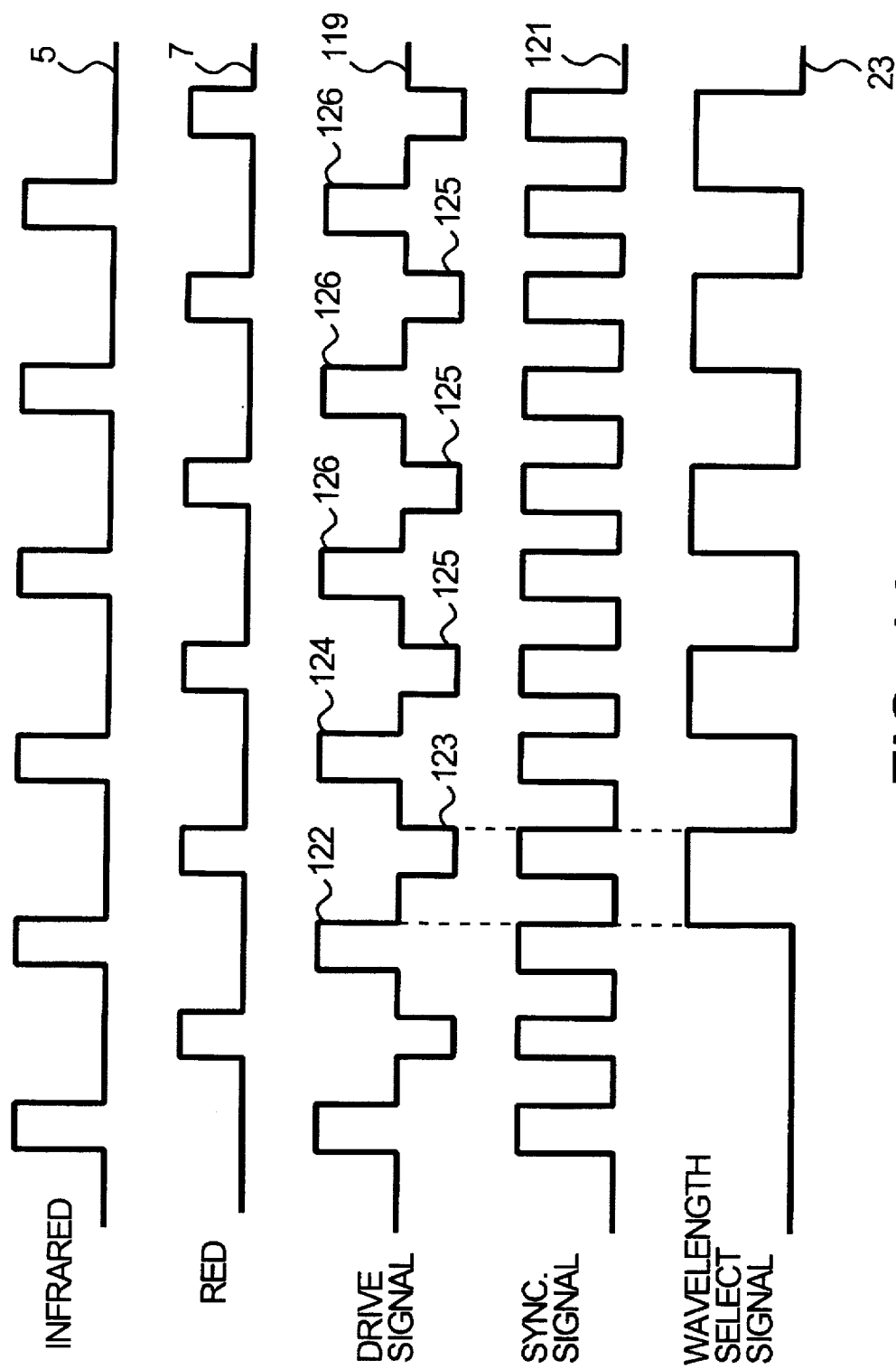
FIG. 14 is a timing diagram illustrating the timing relationships between the light flashes produced by a Nellcor model N-100 pulse oximeter, the drive signal applied to the light emitting diodes of the N-100 oximeter, and the electrical signals produced by the apparatus of FIG. 13.

The timing diagram of FIG. 14 illustrates how microcontroller 16 and switch 24 respond to drive signal 119 to produce selected absorbance signal 25 for the case where pulse oximeter 1 is a Nellcor model N-100. In operating the apparatus of FIG. 13, the user begins by selecting the Nellcor model N-100 from a list of devices displayed on LCD 34. This causes microcontroller 16 to internally select one algorithm from the sequence of instructions stored in memory 38 of FIG. 2, this algorithm being particular to the Nellcor model N-100. Drive signal 119, an amplified version of electrical drive signal 117 produced by oximeter 1, is a bipolar signal which comprises positive-going pulses 122, 124 and 126 when emitter 4 is activated to produce infrared light flashes 5, and negative-going pulses 123 and 125 when emitter 6 is activated to produce red light flashes 7. Synchronization signal 121 interrupts microcontroller 16 each time Nellcor pulse oximeter 1 produces a light flash 5 or 7, causing microcontroller 16 to determine the polarity of drive signal 118 by means of internal ADC 36 shown in FIG. 2.

Referring to FIG. 14, microcontroller 16 determines pulse 122 to be positive-going and so asserts wavelength select signal 23 at the end of pulse 122. Microcontroller 16 thereby selects red absorbance signal 19 via switch 24, which is then conveyed to detector 8 via switch 26, radiating means 28 and prism 29 in response to negative-going pulse 123. Pulse 123 also causes synchronization signal 121 to interrupt microcontroller 16, which responds by setting wavelength select signal 23 low to select infrared absorbance signal 18 via switch 24. Selected absorbance signal 25 so produced by microcontroller 16 and switch 24 is then conveyed to detector 8 via switch 26, radiating means 28 and prism 29 in response to positive-going pulse 124. Once pulse 124 has ended, microcontroller 16 simply toggles wavelength select signal 23 for successive pulses 125 and 126 which follow. Thereby, Nellcor pulse oximeter 1 receives simulated absorbed light 30 which simulates the effect of an anatomical part on light flashes 5 and 7 emitted by Nellcor pulse oximeter 1.

The primary advantage of the apparatus of FIG. 13 over the apparatus of FIG. 1 is that in practise the software algorithms executed by microcontroller 16 for producing wavelength select signal 23 of FIG. 13 are extremely simple compared to the software algorithms for producing wavelength select signal 23 based on time interval, duration and amplitude features of electrical pulse signal 13 of FIG. 1. Compared to the apparatus of FIG. 1, however, the apparatus of FIG. 13 has the limitation that light flashes 5 and 7 emitted by sensor 3 are not detected, and so unlike the apparatus of FIG. 1, the apparatus of FIG. 13 is incapable of producing an indication or alarm signal to the user if one or more of the wavelengths normally emitted by sensor 3 are weak or absent. However, for test applications where the apparatus is simply required to produce predefined oxygen saturation and heart rate indications on oximeter 1, the apparatus of FIG. 13 is sufficient.

In summary, the embodiment shown in FIG. 13 and described above provides useful and novel apparatus for testing a pulsed light oximeter incorporating emitters 4 and 6 activated by electrical drive signal 117, comprising absorbance signal generator 17 for producing a plurality of absorbance signals 18 and 19 representative of the absorbance of an anatomical part, such as the finger of a patient, at the wavelength of each light flash 5 or 7; microcontroller 16 and switch 24 responsive to electrical drive signal 117 for selecting one of absorbance signals 18 or 19 to produce selected absorbance signal 25; and light radiating means 28 responsive to selected absorbance signal 25 for radiating light 30 to detector 8 of oximeter 1 to simulate the effect of the anatomical part on light flashes 5 and 7.

Figure 15:
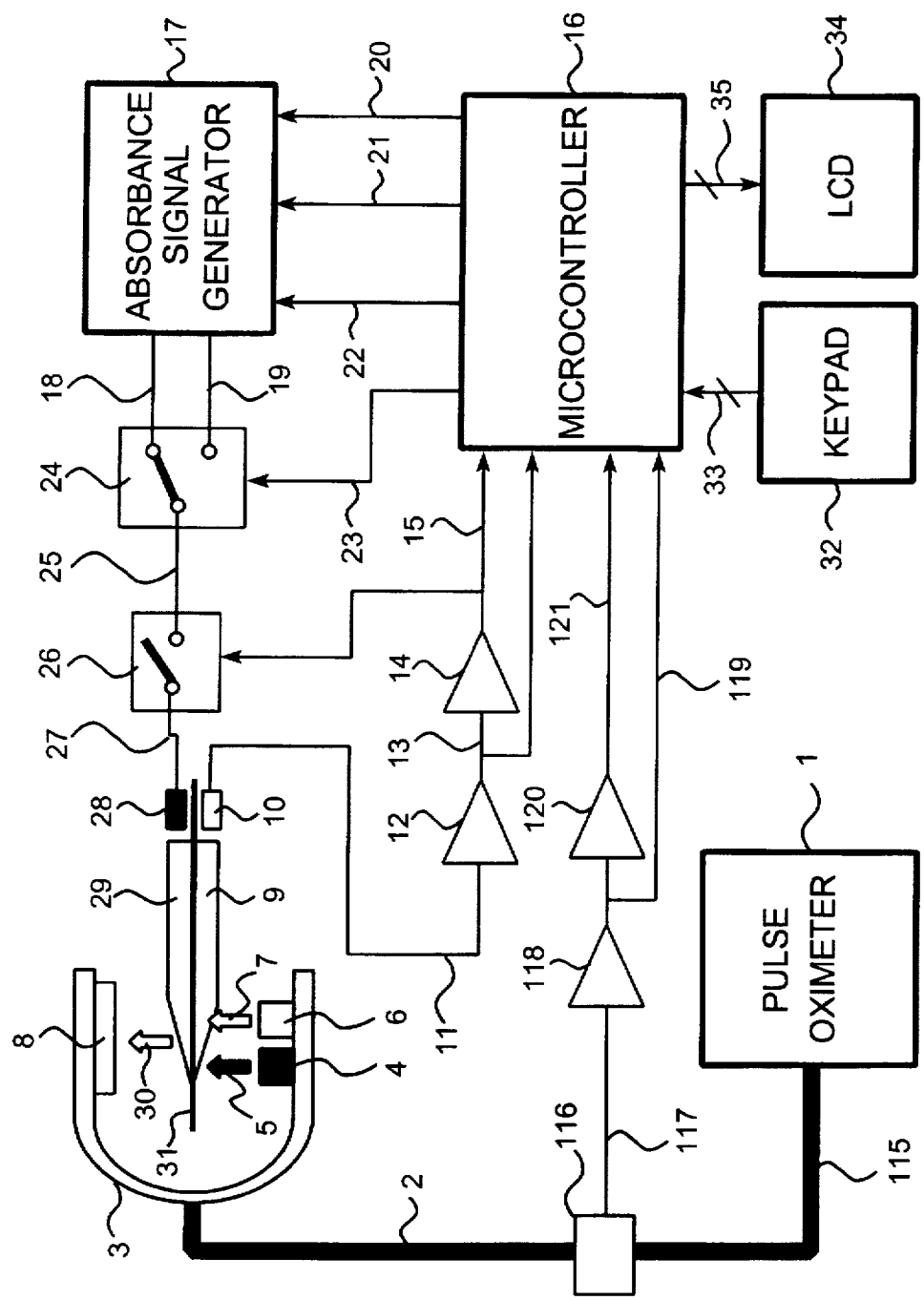
FIG. 15 is a schematic block diagram illustrating a preferred embodiment of the invention for testing a pulsed light oximeter, the oximeter incorporating light emitting diodes which are activated by electrical drive signals.

To overcome the aforementioned limitation of the apparatus of FIG. 13, the apparatus of FIG. 1 may be combined with the apparatus of FIG. 13 to form enhanced apparatus for testing a pulsed light oximeter incorporating light emitting devices activated by electrical drive signals, as is schematically illustrated in the block diagram of FIG. 15.

To provide a user with means for verifying that emitters 4 and 6 of sensor 3 are indeed operating as expected, the apparatus of FIG. 15 includes light sensing means 10 for producing detected light signal 11 representative of light flashes 5 and 7 emitted by sensor 3 of oximeter 1. Microcontroller 16 and LCD 34 provide comparison means for comparing detected light signal 11, in its amplified form as signal 13, with electrical drive signal 117 in its amplified form as signal 119.

Figure 16:
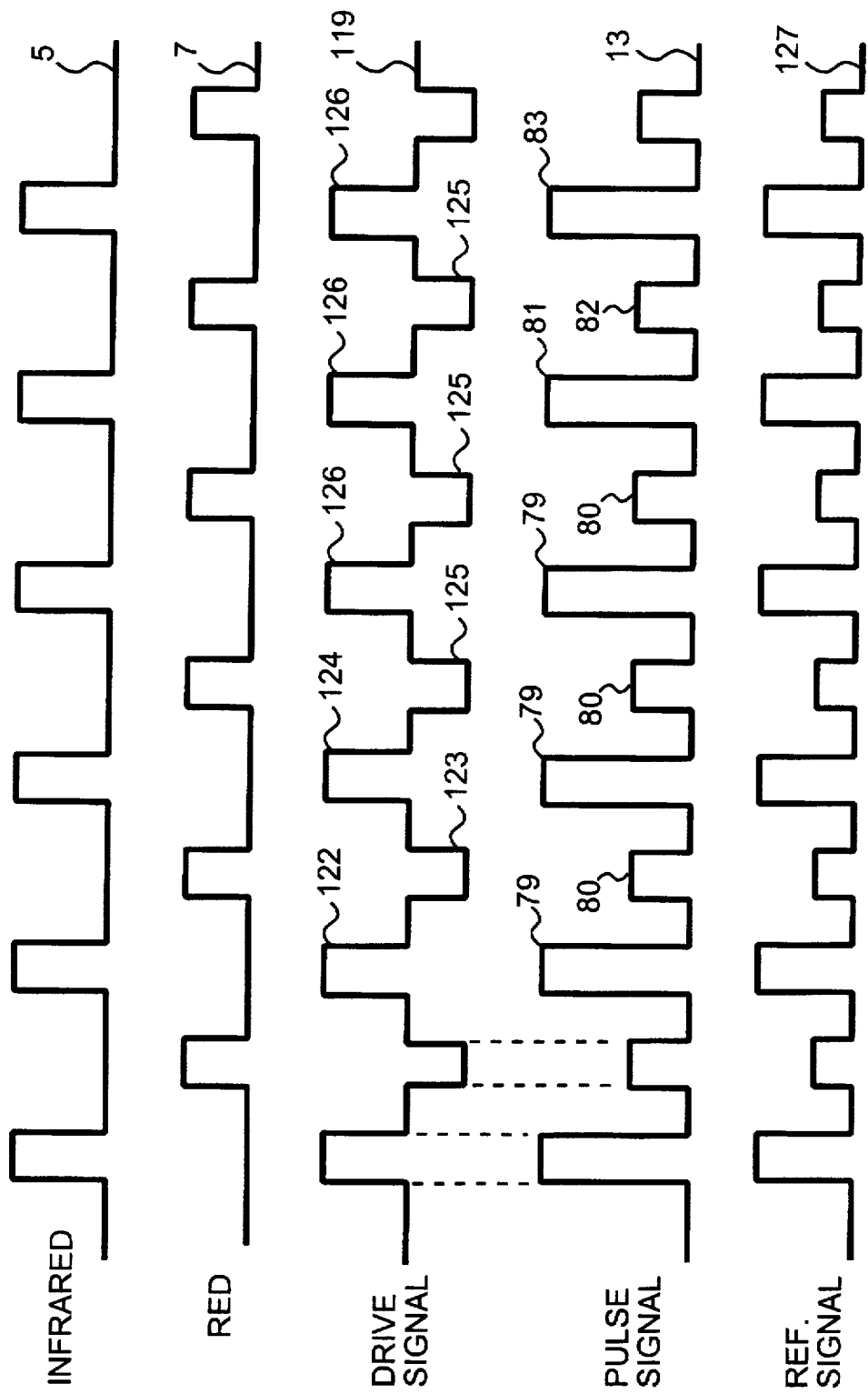
FIG. 16 is a timing diagram illustrating the timing relationships between the light flashes produced by a Nellcor model N-100 pulse oximeter, the drive signal applied to the light emitting diodes of the N-100 oximeter, and the electrical signals produced by the apparatus of FIG. 15.

The timing diagram of FIG. 16 illustrates drive signal 119 and corresponding infrared light flashes 5, red light flashes 7, and pulse signal 13 representative of light flashes 5 and 7 for the case where pulse oximeter 1 is a Nellcor model N-100. FIG. 16 shows that the positive-going pulses 122, 124 and 126 comprising drive signal 119 correspond to infrared light flashes 5 and to larger pulses 79, 81 and 83 of pulse signal 13. FIG. 16 also shows that negative-going pulses 123 and 125 of drive signal 119 correspond to red light flashes 7 and to smaller pulses 80 and 82 of pulse signal 13. In operation, microcontroller 16 may display signals 119 and 13 in real-time to the user by means of LCD 34, and due to the correspondences explained above, thereby allow the user to confirm that both light flashes 5 and 7 are being produced by emitters 4 and 6 respectively. Alternatively, microprocessor 16 may process drive signal 119 to produce characteristic reference signal 127 which is displayed with signal 13 on LCD 34. In this case, the user may more easily compare the features of signal 119, as represented by reference signal 127, to the features of signal 13, and thereby verify that emitters 4 and 6 of sensor 3 are functioning correctly. As suggested by FIG. 16, characteristic reference signal 127 is derived from drive signal 119 by inverting and reducing the amplitude of negative-going pulses 123 and 125 so that a signal comparable to pulse signal 13 is obtained. It should be obvious to those skilled in the art that any number of visual representations of signals 119 and signal 13 on LCD 34 are possible, including representations of signal strength, frequency, and so on, the exact nature of such visual representations being dependent on the diagnostic needs of the user and the time interval, duration and amplitude features of the signals displayed.

Alternatively or in addition to the comparison means provided by microcontroller 16 and LCD 34, microcontroller 16 may produce an alarm signal to the user if signal 13 is not comprised of pulses 79 or 80 corresponding to drive signal pulses 122 or 123 respectively. For example, referring to FIGS. 15 and 16, if red emitter 6 of sensor 3 is defective, red light flashes 7 are not emitted in response to drive signal 117, and so pulses 80 and 82 of signal 13 are not present. Microcontroller 16, triggered by pulses 123 and 125 of signal 119, detects no corresponding pulses in signal 13, and therefore alerts the user by means of an alarm signal. Such an alarm signal could take the form of a literal message posted on LCD 34, such as "SENSOR RED LED DEFECTIVE". Similarly, if infrared emitter 4 of sensor 3 is defective, pulses 79 of signal 13 are absent, causing microcontroller 16 to post the alarm message "SENSOR IR LED DEFECTIVE" on LCD 34. As should be obvious from FIGS. 15 and 16, microcontroller 16 could also analyze drive signal 119 itself and produce an alarm via LCD 34 if either pulses 125 or pulses 126 were missing in drive signal 119. In this case, such alarms could take the form of literal messages such as "MISSING OXIMETER RED DRIVE SIGNAL" or "MISSING OXIMETER IR DRIVE SIGNAL".

Figure 17:
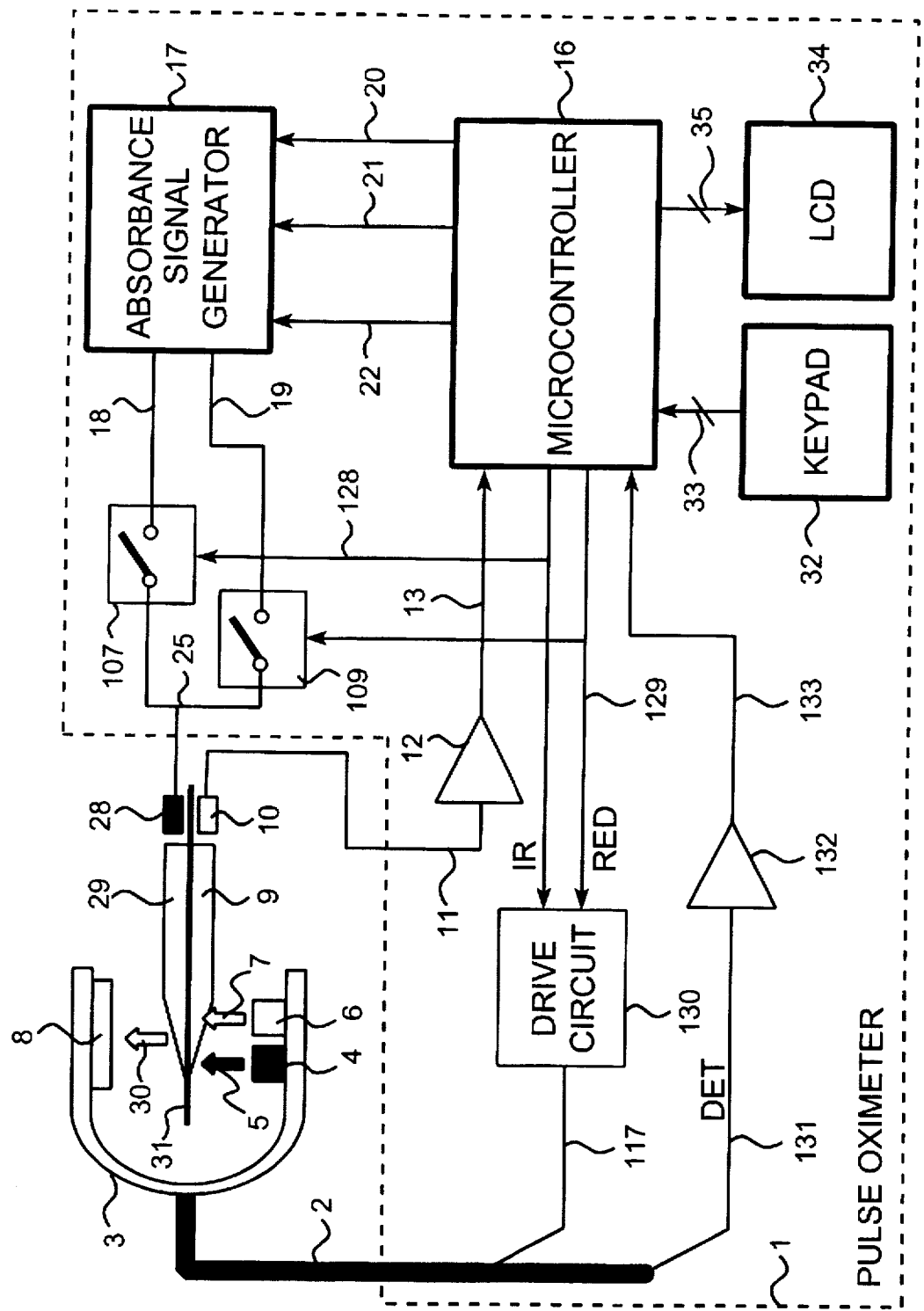
FIG. 17 is a schematic block diagram illustrating how a preferred embodiment of the invention may be incorporated into a pulse oximeter.

FIG. 17 illustrates how various elements of the apparatus appearing in FIGS. 1, 11 and 15 may be integrated as part of pulse oximeter 1, advantageously providing pulse oximeter 1 with superior self-test and sensor diagnostic capabilities. Referring to FIG. 17, microcontroller 16 produces infrared drive signal 128 and red drive signal 129 which are amplified and combined by drive circuit 130 to produce electrical drive signal 117, which as described previously, is conveyed via cable 2 to sensor 3 to activate emitters 4 and 6. Detector signal 131, produced by detector 8 of sensor 3 and conveyed via cable 2, is amplified by signal conditioner 132 to produce amplified detector signal 133 which is input to microcontroller 16.

When sensor 3 is applied to a patient's finger, for example, microcontroller 16 produces drive signals 128 and 129 in a predefined sequence so that sensor 3 emits either infrared light flash 5 or red light flash 7 at any given instant. After light flashes 5 and 7 pass through the patient's finger, detector 8 converts absorbed light flashes to signal 131 which is read as signal 133 by microcontroller 16. Using drive signals 128 and 129 as synchronizing references, microcontroller 16 internally reconstructs absorbance signals representative of the absorbance of the patient's finger at the wavelength of infrared light flashes 5, and the wavelength of red light flashes 7. As explained previously, microcontroller 16 computes the normalized amplitude ratio of the time-varying components of the internally-reconstructed red and infrared absorbance signals, and thereby derives estimates of the patient's blood oxygen saturation and heart rate which are displayed by means of LCD 34.

To activate the self-test mode of pulse oximeter 1, the user may command microcontroller 16 via keypad 32 to begin operating absorbance signal generator 17 by means of signals 20, 21 and 22, such operation being previously described for the apparatus of FIG. 1. Instead of applying sensor 3 to a patient, however, the user applies sensor 3 to the probe apparatus comprising prisms 9 and 29, barrier 31, sensing means 10 and radiating means 28 as shown in FIG. 17. Similar to the approach described for the apparatus of FIGS. 13 and 15, infrared drive signal 128 directly selects infrared absorbance signal 18 by means of analog switch 107, and red drive signal 129 directly selects red absorbance signal 19 by means of analog switch 109 to produce selected absorbance signal 25. Thereby, detector 8 receives simulated absorbed light 30 by means of radiating means 28 and prism 29, detector 8 converting light 30 to amplified detector signal 133 by means of conditioner 132. As described above, microcontroller 16 internally reconstructs signals analogous to infrared absorbance signal 18 and red absorbance signal 19 and produces corresponding blood oxygen saturation and heart rate indications on LCD 34. The amplitude and frequency of absorbance signals 18 and 19 are preselected so that LCD 34 displays predefined oxygen saturation and heart rate, advantageously enabling the user to confirm that drive signals 128 and 129, detector 8, cable 2, and signal conditioner 132 are all functioning normally according to their design.

The testing apparatus of FIG. 17 also includes prism 9, light sensing means 10 and signal conditioner 12. As described previously for the apparatus of FIG. 1, sensing means 10 produces detected light signal 11 which is amplified by conditioner 12 to produce electrical pulse signal 13. Microcontroller 16 compares electrical pulse signal 13, received from sensing means 10 and representative of light flashes 5 and 7, to signals 128 and 129 output from microcontroller 16. In so comparing, microcontroller 16 may display signals 128, 129 and 13 on LCD 34, thereby allowing the user to confirm that emitters 4 and 6 are producing light flashes 5 and 7 respectively. Alternatively or additionally, microcontroller 16 may produce an alarm signal via LCD 34 if signal 13 is not comprised of pulses corresponding to the pulses of drive signals 128 and 129. Advantageously, this enables the user to confirm that drive circuit 130, cable 2, emitter 4 and emitter 6 are all functioning normally according to their design.

Novel apparatus for testing a pulsed light oximeter that provides multi-wavelength capability and an improved probe with low position sensitivity has been described. It is evident that given the preceding description of the preferred embodiment, persons skilled in the art may now make numerous uses of, modifications of, and departures from the preferred embodiment of the invention without departing from the principles of the invention. In light of the foregoing and other examples, the invention is therefore not limited to the details given herein, but may be modified within the scope of the appended claims.

We claim:

1. Apparatus for testing a pulsed light oximeter, comprising:
    (a) light sensing means for producing an electrical pulse signal representative of light flashes emitted by the oximeter, each light flash emitted having one of a plurality of predefined wavelengths;
    (b) signal generating means for producing a plurality of absorbance signals, each absorbance signal representing the optical absorbance of an anatomical part at the wavelength of each light flash;
    (c) selecting means for analyzing one or more features of the electrical pulse signal and for selecting the absorbance signal corresponding to each light flash emitted to produce a selected absorbance signal; and
    (d) light radiating means responsive to the selected absorbance signal for radiating light to the oximeter to simulate the effect of the anatomical part on the light flashes emitted by the oximeter.

2. Apparatus as defined in claim 1 wherein the feature analyzed is the time interval between individual pulses which comprise the electrical pulse signal.

3. Apparatus as defined in claim 1 wherein the feature analyzed is the duration of individual pulses which comprise the electrical pulse signal.

4. Apparatus as defined in claim 1 wherein the feature analyzed is the amplitude of individual pulses which comprise the electrical pulse signal.

5. Apparatus as defined in claim 4 wherein the light radiating means radiates light of a preselected intensity so as to make the oximeter emit different amplitudes of light at each wavelength.

6. Apparatus as defined in claim 1 wherein the features analyzed comprise a combination of the time interval between, the duration of, or the amplitude of individual pulses which comprise the electrical pulse signal.

7. Apparatus as defined in claim 1 wherein the selecting means includes means for producing an alarm signal if the features of the electrical pulse signal do not match predefined reference features derived from a priori knowledge of the oximeter.

8. Apparatus as defined in claim 1 wherein the amplitude of each absorbance signal of the plurality is preselected to produce a predefined oxygen saturation indication on the oximeter.

9. Apparatus as defined in claim 8 wherein each absorbance signal of the plurality comprises a static component representative of tissue and venous blood in the anatomical part, and a time-varying component representative of arterial blood flow through the anatomical part.

10. Apparatus as defined in claim 9 wherein the oximeter is a two-wavelength pulse oximeter and the plurality of absorbance signals comprises the absorbance of the anatomical part near the wavelength of red light, and the absorbance of the anatomical part near the wavelength of infrared light.

11. Apparatus as defined in claim 10 wherein the the frequency of the time-varying component of each absorbance signal is preselected to produce a predefined heart rate indication on the oximeter.

12. A probe for use in testing an oximeter having a transilluminating sensor with light emitting and light detecting elements, comprising:
  (a) a light sensing means for producing a detected light signal representative of light emitted by the sensor;
  (b) a prism for conducting light from the emitting element to the light sensing means, the prism having refractive index greater than air and having one end in the shape of an acute wedge, the wedge having a roughened surface to scatter throughout the wedge the light impingent upon it from the emitting element;
  (c) a light radiating means for producing light in response to a signal representative of light to be received by the sensor;
  (d) a prism for conducting light produced by the radiating means to the detecting element, the prism having refractive index greater than air and having one end in the shape of an acute wedge, the wedge having a roughened surface to disperse over the detecting element the light conducted from the radiating means; and
  (e) a shell for containing the prisms, substantially in the shape of an anatomical part, and including two internal cavities open at the distal end to receive the wedges of the prisms, the cavities separated by a barrier to prevent light transmittance between the radiating means and the sensing means, and between the prisms.

13. Apparatus as defined in claim 12 wherein the barrier additionally prevents light transmittance between the light emitting and light detecting elements of the sensor.

14. Apparatus as defined in claim 13 wherein the barrier includes a planar flange which is wider than the prisms and which is oriented parallel to the prisms.

15. Apparatus as defined in claim 12 wherein the shape of the anatomical part is substantially equivalent to the shape of a human digit.

16. Apparatus as defined in claim 15 wherein the acuteness of the wedges of the prisms is such that the thickness of the probe is not greater than the thickness of a human digit.

17. Apparatus as defined in claim 12 and including a light sensitive element located proximal to the radiating means for producing an alarm signal should the sensor be applied to the probe with incorrect orientation.

18. Apparatus as defined in claim 12 and including display means for displaying the detected light signal to an operator.

19. Apparatus for testing a pulsed light oximeter which emits light flashes, each light flash having one of a plurality of predefined wavelengths, comprising:
  (a) light sensing means for producing a synchronization signal representative of light flashes emitted at one of the predefined wavelengths;
  (b) signal generating means for producing a plurality of absorbance signals, each absorbance signal representing the optical absorbance of an anatomical part at the wavelength of each light flash;
  (c) selecting means responsive to the timing features of the synchronization signal for selecting the absorbance signal corresponding to each light flash emitted, to produce a selected absorbance signal; and
  (d) light radiating means responsive to the selected absorbance signal for radiating light to the oximeter to simulate the effect of the anatomical part on the light flashes emitted by the oximeter.

20. Apparatus as defined in claim 19 wherein the amplitude of each absorbance signal is preselected to produce a predefined oxygen saturation indication on the oximeter.

21. Apparatus as defined in claim 20 wherein the oximeter is a two-wavelength pulse oximeter and the plurality of absorbance signals comprises the absorbance of the anatomical part near the wavelength of red light, and the absorbance of the anatomical part near the wavelength of infrared light.

22. Apparatus as defined in claim 21 wherein the the frequency of each absorbance signal is preselected to produce a predefined heart rate indication on the oximeter.

23. Apparatus for testing a pulsed light oximeter incorporating light emitting devices activated by electrical drive signals, each device emitting a light flash of predefined wavelength in response to a corresponding drive signal, comprising:
  (a) signal generating means for producing a plurality of absorbance signals, each absorbance signal representing the optical absorbance of an anatomical part at the wavelength of each light flash;
  (b) selecting means responsive to the electrical drive signals for selecting the absorbance signal corresponding to each light flash emitted, to produce a selected absorbance signal; and
  (c) light radiating means responsive to the selected absorbance signal for radiating light to the oximeter to simulate the effect of the anatomical part on the light flashes emitted by the oximeter.

24. Apparatus as defined in claim 23 wherein the amplitude of each absorbance signal is preselected to produce a predefined oxygen saturation indication on the oximeter.

25. Apparatus as defined in claim 24 wherein the oximeter is a two-wavelength pulse oximeter and the plurality of absorbance signals comprises the absorbance of the anatomical part near the wavelength of red light, and the absorbance of the anatomical part near the wavelength of infrared light.

26. Apparatus as defined in claim 25 wherein the the frequency of each absorbance signal is preselected to produce a predefined heart rate indication on the oximeter.

27. Apparatus as defined in claim 23 wherein the apparatus comprises a part of the oximeter.

28. Apparatus for testing a pulsed light oximeter incorporating light emitting devices activated by electrical drive signals, each device emitting a light flash of predefined wavelength in response to a corresponding drive signal, comprising:

(a) signal generating means for producing a plurality of absorbance signals, each absorbance signal representing the optical absorbance of an anatomical part at the wavelength of each light flash;

(b) selecting means responsive to the electrical drive signals for selecting the absorbance signal corresponding to each light flash emitted, to produce a selected absorbance signal;

(c) light radiating means responsive to the selected absorbance signal for radiating light to the oximeter to simulate the effect of the anatomical part on the light flashes emitted by the oximeter;

(d) light sensing means for producing a detected light signal representative of light flashes emitted by the oximeter; and (e) comparison means for comparing the detected light signal with the electrical drive signals.

29. Apparatus as defined in claim 28 wherein the comparison means also produces an alarm signal if the detected light signal is not comprised of signals corresponding to the electrical drive signals.

30. Apparatus as defined in claim 29 wherein the amplitude of each absorbance signal is preselected to produce a predefined oxygen saturation indication on the oximeter.

31. Apparatus as defined in claim 30 wherein the oximeter is a two-wavelength pulse oximeter and the plurality of absorbance signals comprises the absorbance of the anatomical part near the wavelength of red light, and the absorbance of the anatomical part near the wavelength of infrared light.

32. Apparatus as defined in claim 31 wherein the the frequency of each absorbance signal is preselected to produce a predefined heart rate indication on the oximeter.

33. Apparatus as defined in claim 28 wherein the apparatus comprises a part of the oximeter.

* * * * *